(12) United States Patent
Johnson et al.

(10) Patent No.: US 6,812,332 B2
(45) Date of Patent: Nov. 2, 2004

(54) CHROMOGENIC SUBSTRATES OF SIALIDASE AND METHODS OF MAKING AND USING THE SAME

(75) Inventors: Stephen C. Johnson, Birmingham, AL (US); Ashraf Saeed, Birmingham, AL (US); Ming Luo, Birmingham, AL (US)

(73) Assignees: IBBEX, Inc., Birmingham, AL (US); UAB Research Foundation, Birmingham, AL (US)

(*) Notice: Subject to any disclaimer, the term of this patent is extended or adjusted under 35 U.S.C. 154(b) by 0 days.

(21) Appl. No.: 10/348,668

(22) Filed: Jan. 21, 2003

(65) Prior Publication Data
US 2003/0162240 A1 Aug. 28, 2003

Related U.S. Application Data

(62) Division of application No. 10/328,790, filed on Dec. 24, 2002, which is a division of application No. 09/651,622, filed on Aug. 3, 2000, now Pat. No. 6,512,100, which is a continuation of application No. 08/958,356, filed on Oct. 27, 1997, now abandoned, each is a division of application No. 08/958,356.

(51) Int. Cl.$^7$ .................. C07H 15/04; C07H 17/04; A61K 31/70

(52) U.S. Cl. ............. 536/17.2; 536/17.3; 536/17.4; 536/17.7; 536/17.8; 536/17.9; 536/18.1; 536/18.4; 514/25; 514/23; 514/62; 435/5; 435/7.1; 435/200

(58) Field of Search ............... 536/17.2, 17.3, 536/17.4, 17.7, 17.8, 17.9, 18.1, 18.4; 514/25, 23, 62; 435/6, 7.1, 15, 200

(56) References Cited

U.S. PATENT DOCUMENTS

| | | |
|---|---|---|
| 3,950,322 A | 4/1976 | Thomas et al. |
| 4,351,823 A | 9/1982 | Rubin |
| 4,994,376 A | 2/1991 | Zambon et al. |
| 5,663,055 A | 9/1997 | Turner et al. |

FOREIGN PATENT DOCUMENTS

| | | |
|---|---|---|
| EP | 0413561 | 2/1991 |
| GB | 2008103 | 5/1979 |
| JP | 02088594 | 3/1990 |
| JP | 05339283 | 12/1993 |
| JP | 06067956 | 8/1994 |
| WO | 9109975 | 12/1990 |
| WO | 9212256 | 7/1992 |
| WO | 0024753 | 5/2000 |

OTHER PUBLICATIONS

Hirst, G.K. (1941) "The Agglutination of Red Blood Cells by Allontoic Fluid of Chick Embryos Infected with Influenza Virus" Science 94(2427):22–23.

Gornati, Rosalba, Subhash Basu, Giovanni Bernardini, Angela M. Rizzo, Federica Rossi, Bruno Berra (1997) "Activities of flycolipid glycosyltransferases and sialidases during the early development of *Xenopus laevis*" 166:117–124.

(List continued on next page.)

Primary Examiner—James O. Wilson
Assistant Examiner—Devesh Khare
(74) Attorney, Agent, or Firm—Saliwanchik, Lloyd & Saliwanchik

(57) ABSTRACT

The subject invention discloses materials and methods for the design, synthesis, and biochemical evaluation of chromogenic substrate compounds for sialidases of bacterial, viral, protozoa, and vertebrate (including humans) origin. In particular, this invention provides a novel class of effective compounds as chromogenic substrates of these sialidases which yield chromogenic products after reactions catalyzed by sialidase take place. Also provided are methods of making these substrate compounds, methods of diagnosis and prognosis of sialidase related diseases using these substrate compounds.

23 Claims, 12 Drawing Sheets

(1 of 12 Drawing Sheet(s) Filed in Color)

OTHER PUBLICATIONS

Cacalano, Grace, Maureen Kays, Lisa Salman, Alice Prince (1992) "Production of the *Pseudomonas aeruginosa* Neuraminidase Is Increased under Hyperosmolar Condtions and Is Regulated by Genes Involved in Alginate Expression" J. Clin. Invest. 891866–1874.

Bratosin et al. (1995) "Flow cytofluroimetric analysis of young and senescent human erythrocytes probed with lactins. Evidence that sialis acids control their life span" Glycoconjugate Journal 12:258–267.

Liu, Chongguang, Maryna C. Eichelberger, Richard W. Compans, Gillian M. Air (1995) "Influenza Type A Virus Neuraminidase Does Not Play A Role In Viral Entry, Replication, Assembly or Budding" Journal of Virology 69(2):1099–1106.

Liljemark, William F., Cynthia G. Bloomquist, Laurie J. Fenner, Patrick J. Antonelli, M. Cecilia Coulter (1989) "Effect of Neuraminidase on the Adherence to Salivary Pellicle of *Streptococcus sanguis* and *Streptococcus mitis*" Caries Res. 23:141–145.

Ashwell et al. (1992) "Pathways for the hydrolysis of glycosides of N–acetylneuraminic acid" *J. Am. Chem. Soc.* 114:10158–10166.

Palese, P., D. Bucher, E.D. Kilbourne (Feb. 1973) "Applications of a Synthetic Neuraminidase Substrate" *Applied Microbiology* 25(2):195–201.

Baumberger, Franz and Andrea Vasella (1986) "4–Methylumbelliferyl 5–Acetamido–3,4,5–trieoxy–α–D–manno–2–nonulopyranosidionic Acid: Synthesis and Resistance to Bacterial Sialidases" *Helvetica Chimica Acta* 69:1927–1935.

Zbiral, Erich, Erwin Schreimer, Mamikrao M. Salunkhe, Gerhard Schulz, Reinhard G. Kleineidam, Roland Schauer (1989) "Synthesis of the 4–Methylumbelliferyl 2α–Glycosides of 7–Epi–, 8–Epi–, and 7,8–Bis(epi)–N–acetylneuraminic Acids, as well as of 7–Deoxy–, 8–Deoxy–, 9–Deoxy–, and 4.7–Dideoxy–N–acetylneuraminic Acids and Their Behaviour Towards Sialidase from *Vibrio cholerae*" *Liebigs Ann. Chem.* pp. 519–526.

Sigma catalog, 1993 edition, p. 33.

Briselden, Ann Marie, Bernard J. Moncia, Claire E. Stevens, Sharon L. Hillier (1992) "Sialidases (Neuraminidases) in Bacterial Vaginosis and Bacterial Vaginosis–Associated Microflora" J. Clinical Microbiology 30(3):663–666.

Bonten, Erik, Aarnoud van der Spoel, Maarten Forerod, Gerard Grosveld, Alessandra d'Azzo (1996) "Characterization of human lysosomal neuraminidase defines the molecular basis of the metabolic storage disorder sialidosis" Genes & Development 10:3156–3169.

Cross, George A.M. Garry S. Takle (1993) "The Surface Trans–sialidase Family Of *Trypanosoma Cruzi*" Ann. Rev. Microbiology 47:385–411.

Crennell, Susan, Elspeth Garman, Graeme Laver, Eric Vimr, Garry Taylor (1994) "Crystal structure of *Vibrio cholerae* neuraminidase reveals dual lectin–like domains in addition to the catalytic domain" Structure 2(6):535–44.

Crennell, Susan J., Elspeth F. Garman, W. Graeme Laver, Eric R. Vimr, Garry L. Taylor (1993) "Crystal structure of a bacterial sialidase (from *Salmonella typhimurium* LT2) shows the same fold as an influenza virus neuraminidase" Proc. Natl. Acad. Sci. USA 90:9852–9856.

Lentz, Michael R., Robert G. Webster, Gillian M. Air (1987) "Site–Directed Mutation of the Active Site of Influenza Neuraminidase and Implications for the Catalytic Mechanism" Biochemistry 26:(17):5351–5358.

Cabezas, et al. (1980) "Nueraminidase from influenza virus A (H3N2)" *Biochim. Et Biophys. Acta* 616:228–238.

Aamlid, Kai H., Grantham Lee, Brian V. Smith, Anthony C. Richardson, Robert G. Price (1990) "New colorimetric substrates for the assay of glycosidases" Carbohydrate Research 205;c5–c9.

Baggett, Neil and Brian J. Marsden (1982) "Reinvestigation Of The Synthesis Of 4–Methylcoumarin–7–YL 5–Acetamido–3, 5–Dideoxyα–D–glycero–D–galacto–2–Nonulopyranosidonic Acid, A Fluorogenic Substrate For Neuraminidase" Carbohydrate Research 110:11–18.

Eschenfelder, Volker and Reinhard Brossmer (1987) "Synthesis of p–nitrophenyl 5–acetamido– 3, 5–dideoxy–α–D–Glycero–D–galacto–2– nonulopyranosidonic acid, a chromogenic substrate for sialidases" Carbohydr. Res. 162:294–297.

Eschenfelder, Volker and Reinhard Brossmir (1987) "5–Bromo–indol–3–yl 5–Acetamido–3, 5–dideoxy–α–D–glycero–D–galactononulpyranosidonic Acid, a Novel Chromogenic Substrate for the Staining of Sialidase Activity" Glycoconjugate J. 4:171–178.

Freudenberg, K. H. Resnik, H. Boesenberg, D. Rasenack (1952) "Das an der Verholzung Beteiligte Fermentsystem" Chem. Ber. 85:641–647.

Holmquist, L., R. Brossmer (1972) "Specificity of neuraminidase, synthesis and properties of the 2–aminoethyl α–and the 2–pyridyl α–and β–glycosides of N–acetyl–D–neuraminic acid" Hoppe–Seyler's Z. Physiol. Chem. 353:1346–1350.

Sinnott et al. (1993) "Leech sialidase L cleaves the glycon–aglycon bond with the substrate in a normally disfavored conformation" *J. Am. Chem. Soc.* 115:3334–3335.

Horwitz, J.P., J. Chua, R.J. Curby, A.J. Tomson, M.A. Darooge, B.E. Fisher, J. Mauricio, I. Klundt (1964) "Substrates for Cytochemical Demonstration of Enzyme Activity. I. Some Substituted 3–Indoyl–β–D–glycopyranosides" J. Med. Chem. 7:574–575.

de Kiewiet, T.E., H. Stephen (1931) "Z–Hydroxy–4–methoxy–and 4–Hydroxy–2–methoxy–benzaldehydes" J. Chem. Soc. 133:84–85.

Kuhn, Richard, Peter Lutz and Donald L. MacDonald (1966) "Synthase anomerer Salinsauremethylketoside" Chem. Ber. 99:611–617.

Ley, Arthur Newton, Raymond John Bowers, Saul Wolfe (1988) "Indoxyl–β–D–glucuronide, a novel chromogenic reagent for the specific detection and enumeration of *Escherichia coli* in environmental samples" Can. J. Microbiol. 34:690–693.

Myers, R. W., R. T. Lee, Y. C. Lee, G. H. Thomas, L. W. Reynolds, Y. Uchida (1980) "The Synthesis of 4–Methylumbelliferyl α–Ketoside of N–Acetylneuraminic Acid and its Use in a Fluorometric Assay for Neuraminidase" Anal. Biochem. 101:166–174.

Ogura, Haruo and Kimio Furuhata (1986) "Syntheses of 2–O–Glycosyl Derivatives of N–Acetyl–D–Neuraminic Acid" Carbohydrate Research 158:37–51.

Lehninger (1975) Biochemistry, $2^{nd}$ edition, p. 594, Worth Publishers, Inc. New York.

Okamoto, Kaoru, and Toshio Goto (1990) "Glycosidation Of Sialic Acid" Tetrahedron 46(17):5835–5857.

Patel, Atula and Anthony C. Richardson (1986) "3–Methoxy–4–(2–Nitrovinyl)Phenyl Glycosides As Potential Chromogenic Substrates For The Assay Of Glycosidases" Carbohydrate Research 146:241–249.

Paulsen, Hans and Peter Matschulat (1991) "Synthese von C–Glycosiden der N–Acetylneuraminsaure und weiteren Derivaten" Liebigs Ann. Chem. 487–495.

Robertson, Alexander (1927) "Syntheses of Glucosides. Part I. The Synthesis of Indican" J. Chem. Soc. 1937–1943.

Tiemann, F., P. Koppe (1881) "Ueber die Darstellung von Protocatechualdehyd aus Brenzcatechin, sowie einige Derivate des Guajacols und Kreosols" Chem Ber. 14:2015–2028.

Warner, Thomas G. and John S. O'Brien (1979) "Synthesis of 2' –(4–Methylumbelliferyl)–α–D–N–acetylneuraminic Acid and Detection of Skin Fibroblast Neuraminidase in Normal Humans and in Sialidosis" Biochemistry 18(13):2783–2787.

Anderson, F.B. and D.H. Leaback (1961) "Substrates For The Histochemical Localization Of Some Glycosidases" Tetrahedron 12:236–239.

CHROMOGENIC SUBSTRATES OF SIALIDASE AND METHODS OF MAKING AND USING THE SAME

CROSS-REFERENCE TO RELATED APPLICATION

This application is a divisional of application Ser. No. 10/328,790, filed Dec. 24, 2002, which is a divisional of application Ser. No. 09/651,622, filed Aug. 30, 2000, now U.S. Pat. No. 6,512,100 B1 which is a continuation of application Ser. No. 08/958,356, filed Oct. 27, 1997, now abandoned. This application is also a divisional of application Ser. No. 08/958,356, filed Oct. 27, 1997, now abandoned. Each of these applications is hereby incorporated by reference in their entireties, including any figures, tables, and drawings.

The research related to this invention is in part supported by a contract from the University of Alabama at Birmingham as a grant from the US Defense Advanced Research Projects Agency, grant number MDA 972-97-K-0002.

FIELD OF THE INVENTION

The current invention relates to the design, synthesis, and biochemical evaluation of chromogenic substrate compounds for sialidases of bacterial, viral, protozoa, and vertebrate (including humans) origin. In particular, this invention provides a novel class of effective compounds as chromogenic substrates of these sialidases which yield chromogenic products after reactions catalyzed by sialidase take place. Also provided are methods of making these substrate compounds, methods of diagnosis and prognosis of sialidase related diseases using these substrate compounds.

BACKGROUND OF THE INVENTION

Sialidase (EC, 3.2.1.18, also known as neuraminidase, acylneuraminyl hydrolase) is a protein enzyme produced by many organisms such as bacteria, viruses, protozoa, and vertebrates including humans (Hirst, G. K. [1941] *Science* 94:22–23). This class of enzymes catalyzes the hydrolysis of a terminal sialic acid which is linked to oligosaccharides through an O-glycosidic bond. Crystal structure of sialidases showed that the enzyme has a highly conserved active site centered in a propeller like β-sheet twirl (Crennell, S. J. et al. [1993] *Proc. Natl. Acad. Sci. USA* 90:9852–9856).

Sialidases perform many critical biological functions. In bacteria, sialidase helps bacterial adhesion to tissues, and provides additional nutritional sources (Crennell, S. et al. [1994] *Structure* 2(6):535–544). In viruses, it helps the release of progeny viruses (Liu, C. et al. [1995] *J. Virol.* 69:1099–1106). In a parasite, *Trypanosoma cruzi*, a sialidase (also known as trans-sialidase) removes sialic acids from infected cells and decorates its own surface with these sialic acids. In humans, sialidases are involved in protein digestion, immune responses, and cell proliferation. Abnormal production of sialidases may lead to serious human diseases such as sialidosis or increased *Pseudomonas aeruginosa* infection in cystic fibrosis patients.

Since sialidases are associated with many diseases, a color-producing substrate of sialidase would be an excellent diagnostic or prognostic reagent for sialidase-related diseases. For instance, sialidase level is elevated in bacterial vaginosis (Briselden, A. M. et al. [1992] *J. Clin. Microbiol.* 30:663–666). Measurement of sialidase level in the vaginal samples could be used to diagnose bacterial vaginosis. In periodontal disease caused by bacterial infection, it has been shown that presence of sialidase increases the colonization of harmful bacteria (Liljemark, W. F. et al. [1989] *Caries Res.* 23:141–145). The cell invasion form of *T. cruzi*, Trypomastigote, expresses high levels of trans-sialidase activity; therefore, measurement of trans-sialidase level could be used for diagnosis of *T. cruzi* infection and for monitoring disease progress (Cross, G. A., G. B. Takle [1993] *Annu. Rev. Microbiol.* 47:385–411). In cystic fibrosis patients, *Pseudomonas aeruginosa* infection is one of the leading causes of death. Sialidase was shown to be involved in the disease progress (Cacalano, G. et al. [1992] *J. Clin. Invest.* 89:1866–1874). Sialidase is also related to the regulation of cell proliferation (Bratosin, D. et al. [1995] *Glycoconj. J.* 12:258–267), the clearance of plasma proteins (Bonten, E. et al. [1996] *Genes & Devel.* 10:3156–3169), and the catabolism of gangliosides and glycoproteins (Gornati, R. et al. [1997] *Mol. Cell Biochem.* 166:117–124).

Currently, there is available a synthetic substrate of sialidase, 4-methylumbelliferyl-B-acetyl-neuraminic acid (4-MUN) (Lentz, M. R., R. G. Webster, G. M. Air [1987] *Biochemistry* 26:5351–5358), which produces a product with characteristic fluorescence spectrum upon hydrolysis. This change of fluorescence spectrum can only be measured with a specialized instrument (fluorospectrometer). The substrate compounds of the current invention produce a visible color change upon hydrolysis, which is highly advantageous in medical diagnostic applications.

BRIEF SUMMARY OF THE INVENTION

In one embodiment, the current invention relates to the design and synthesis of novel chromogenic substrate compounds for sialidases. In another embodiment, the subject invention pertains to the use of the novel chromogenic substrates in assays for the detection of sialidases. The sialidases which are detected using the procedures and compounds of the subject invention are of bacterial, viral, protozoa, and vertebrate (including human) origin. In a specific embodiment, the subject invention provides a novel class of compounds which are useful as chromogenic substrates of sialidases.

In one embodiment, the present invention provides chromogenic sialidase substrate compounds having the following formula:

General Structure I

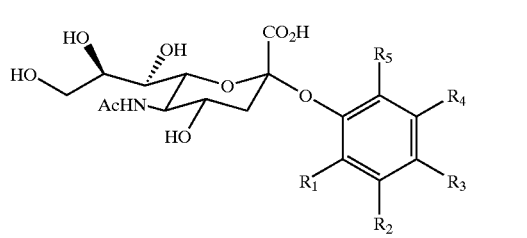

wherein, $R_1$=H, $R_6$, $OR_6$, $OC(O)R_7$, $NO_2$, $NH_2$, $N(R_6)_2$, $NHC(O)R_6$, $NHC(O)OR_6$, Cl, Br, I, F, CHO, $CO_2R_6$, $C(O)N(R_6)_2$, $C(N\sim OH)NH_2$, $OPO_3R_6$, $OPO_2(CH_2)_jCH_3$, $CH_2PO_3R_6$, $OSO_3R_6$, $OSO_2(CH_2)_jCH_3$, $CH_2SO_3R_6$, or CN, where j is an integer from 0 to 3; wherein $R_2$=H, $R_6$, $OR_6$, $OC(O)R_7$, $NO_2$, $NH_2$, $N(R_6)_2$, $NHC(O)R_6$, $NHC(O)OR_6$, Cl, Br, I, F, CHO, $CO_2R_6$, $C(O)N(R_6)_2$, $C(N\sim OH)NH_2$, $OPO_3R_6$, $OPO_2(CH_2)_jCH_3$, $CH_2PO_3R_6$, $OSO_3R_6$, $OSO_2(CH_2)_jCH_3$, $CH_2SO_3R_6$, or CN, where j is an integer from 0 to 3; wherein $R_4$=H, $R_6$, $OR_6$, $OC(O)R_7$, $NO_2$, $NH_2$, $N(R_6)_2$, $NHC(O)R_6$, $NHC(O)OR_6$, Cl, Br, I, F, CHO, $CO_2R_6$, $C(O)N(R_6)_2$, $C(N\sim OH)NH_2$, $OPO_3R_6$, $OPO_2(CH_2)_jCH_3$, $CH_2PO_3R_6$, $OSO_3R_6$, $OSO_2(CH_2)_jCH_3$, $CH_2SO_3R_6$, or CN, where j is an integer from 0 to 3; wherein $R_5$=H, $R_6$, $OR_6$, $OC(O)R_7$, $NO_2$, $NH_2$, $N(R_6)_2$, $NHC(O)R_6$, $NHC(O)OR_6$, Cl, Br, I, F, CHO, $CO_2R_6$, $C(O)N(R_6)_2$, $C(N\sim OH)NH_2$, $OPO_3R_6$, $OPO_2(CH_2)_jCH_3$, $CH_2PO_3R_6$, $OSO_3R_6$, $OSO_2(CH_2)_jCH_3$, $CH_2SO_3R_6$, or CN, where j is an integer from 0 to 3; wherein, $R_3$=$NO_2$, CHO, $(CR_8=CR_8)_kCN$ or $(CR_8=CR_8)_k NO_2$, where k is an from 1 to 3, or

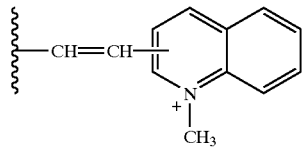

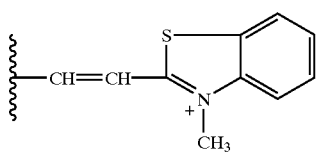

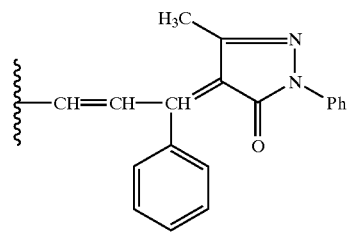

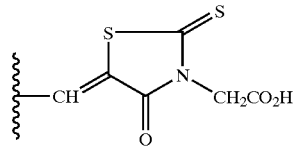

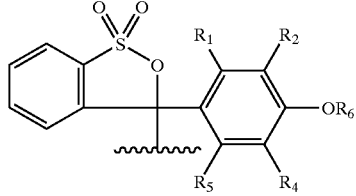

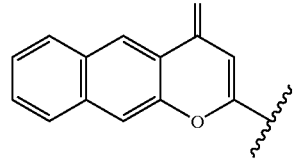

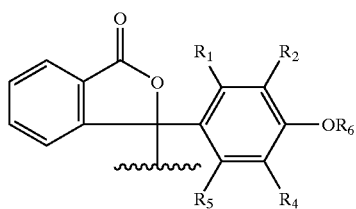

wherein, $R_6$=H, $C(CH_3)_3$, $CH(CH_3)_2$, $CH_2CH(CH_3)_2$, $CH(CH_3)(CH_2)_mCH_3$, or $(CH_2)_mCH_3$, where m is an integer from 0 to 3; wherein, $R_7$=$R_6$, $OR_6$, or $N(R_6)_2$; wherein $R_8$=H or $(CH_2)_nCH_3$; where n is an integer from 0 to 3.

Also provided are chromogenic sialidase substrate compounds having the formula of General Structure I, wherein, $R_1$=H, $R_6$, $OR_6$, $OC(O)R_7$, $NO_2$, $NH_2$, $N(R_6)_2$, Cl, Br, I, F, CHO, $CO_2R_6$, $C(O)N(R_6)_2$, $C(N\sim OH)NH_2$, $OPO_3R_6$, $OPO_2(CH_2)_jCH_3$, $CH_2PO_3R_6$, $OSO_3R_6$, $OSO_2(CH_2)_jCH_3$, $CH_2SO_3R_6$, or CN, where j is an integer from 0 to 3; wherein, $R_2$ or $R_4$=H, $R_6$, $OR_6$, $OC(O)R_7$, $NO_2$, $NH_2$, $N(R_6)_2$, Cl, Br, I, F, CHO, $CO_2R_6$, $C(O)N(R_6)_2$, $C(N\sim OH)NH_2$, $OPO_3R_6$, $OPO_2(CH_2)_jCH_3$, $CH_2PO_3R_6$, $OSO_3R_6$, $OSO_2(CH_2)_jCH_3$, $CH_2SO_3R_6$, or CN, where j is an integer from 0 to 3; wherein, $R_3$=H, $R_6$, $OR_6$, $OC(O)R_7$, $NO_2$, $NH_2$, $N(R_6)_2$, Cl, Br, I, F, CHO, $CO_2R_6$, $C(O)N(R_6)_2$, $C(N\sim OH)NH_2$, $OPO_3R_6$, $OPO_2(CH_2)_jCH_3$, $CH_2PO_3R_6$, $OSO_3R_6$, $OSO_2(CH_2)_jCH_3$, $CH_2SO_3R_6$, or CN, where j is an integer from 0 to 3; wherein, $R_5$=H, $OR_6$, $OC(O)R_7$, $NO_2$, $NH_2$, $N(R_6)_2$, Cl, Br, I, F, CHO, $CO_2R_6$, $C(O)N(R_6)_2$, $C(N\sim OH)NH_2$, $OPO_3R_6$, $OPO_2(CH_2)_jCH_3$, $CH_2PO_3R_6$, $OSO_3R_6$, $OSO_2(CH_2)_jCH_3$, $CH_2SO_3R_6$, or CN, where j is an integer from 0 to 3; wherein, $R_2$ or $R_4$=$NO_2$, CHO, $(CR_8=CR_8)_kCN$ or $(CR_8=CR_8)_kNO_2$, where k is an integer from 1 to 3, or

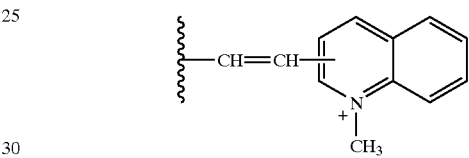

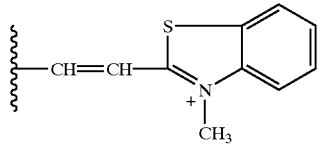

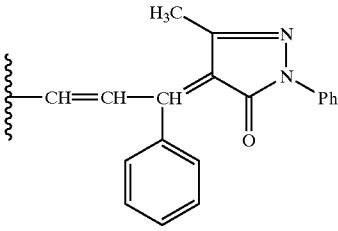

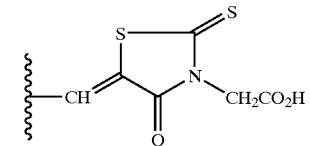

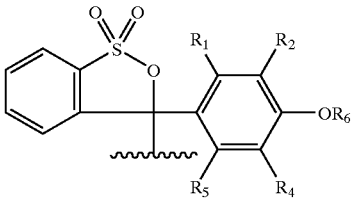

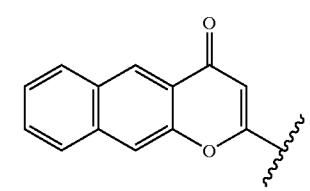

-continued

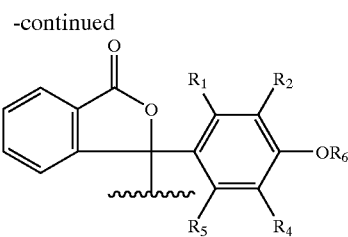

wherein, $R_6$=H, $C(CH_3)_3$, $CH(CH_3)_2$, $CH_2CH(CH_3)_2$, $CH(CH_3)(CH_2)_mCH_3$, or $(CH_2)_mCH_3$, where m is an integer from 0 to 3; wherein, $R_7$=$R_6$, $OR_6$, or $N(R_6)_2$; wherein $R_8$=H or $(CH_2)_nCH_3$; where n is an integer from 0 to 3.

Also provided are chromogenic sialidase substrate compounds having the formula of General Structure I, wherein, $R_1$ or $R_5$=H, $OR_6$, $OC(O)R_7$, $NO_2$, $NH_2$, $N(R_6)_2$, Cl, Br, I, F, CHO, $CO_2R_6$, $C(O)N(R_6)_2$, $C(N\sim OH)NH_2$, $OPO_3R_6$, $OPO_2(CH_2)_jCH_3$, $CH_2PO_3R_6$, $OSO_3R_6$, $OSO_2(CH_2)_jCH_3$, $CH_2SO_3R_6$, or CN, where j is an integer from 0 to 3; wherein, $R_2$=H, $OR_6$, $OC(O)R_7$, $NO_2$, $NH_2$, $N(R_6)_2$, Cl, Br, I, F, CHO, $CO_2R_6$, $C(O)N(R_6)_2$, $C(N\sim OH)NH_2$, $OPO_3R_6$, $OPO_2(CH_2)_jCH_3$, $CH_2PO_3R_6$, $OSO_3R_6$, $OSO_2(CH_2)_jCH_3$, $CH_2SO_3R_6$, or CN, where j is an integer from 0 to 3; wherein, $R_3$=H, $OR_6$, $OC(O)R_7$, $NO_2$, $NH_2$, $N(R_6)_2$, Cl, Br, I, F, CHO, $CO_2R_6$, $C(O)N(R_6)_2$, $C(N\sim OH)NH_2$, $OPO_3R_6$, $OPO_2(CH_2)_jCH_3$, $CH_2PO_3R_6$, $OSO_3R_6$, $OSO_2(CH_2)_jCH_3$, $CH_2SO_3R_6$, or CN, where j is an integer from 0 to 3; wherein, $R_4$=H, $OR_6$, $OC(O)R_7$, $NO_2$, $NH_2$, $N(R_6)_2$, Cl, Br, I, F, CHO, $CO_2R_6$, $C(O)N(R_6)_2$, $C(N\sim OH)NH_2$, $OPO_3R_6$, $OPO_2(CH_2)_jCH_3$, $CH_2PO_3R_6$, $OSO_3R_6$, $OSO_2(CH_2)_jCH_3$, $CH_2SO_3R_6$, or CN, where j is an integer from 0 to 3; wherein $R_1$ or $R_5$=$NO_2$, CHO, $(CR_8=CR_8)_kCN$ or $(CR_8=CR_8)_kNO_2$, where k is an integer from 1 to 3; wherein, $R_6$=H, $C(CH_3)_3$, $CH(CH_3)_2$, $CH_2CH(CH_3)_2$, $CH(CH_3)(CH_2)_mCH_3$, or $(CH_2)_mCH_3$, where m is an integer from 0 to 3; wherein, $R_7$=$R_6$, $OR_6$, or $N(R_6)_2$, wherein $R_8$=H or $(CH_2)_nCH_3$; where n is an integer from 0 to 3.

Also provided are chromogenic sialidase substrate compounds having the following formula:

General Structure II

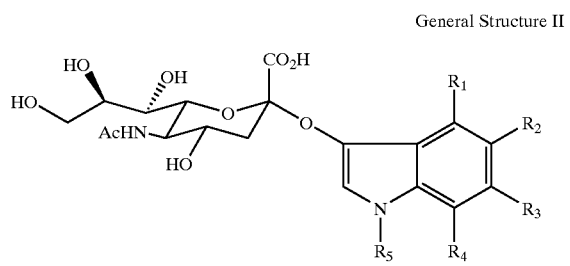

wherein, $R_1$=H, $OR_6$, $OC(O)R_7$, $NO_2$, $NH_2$, $N(R_6)_2$, Cl, Br, I, F, CHO, $CO_2R_6$, $C(O)N(R_6)_2$, $C(N\sim OH)NH_2$, $OPO_3R_6$, $OPO_2(CH_2)_jCH_3$, $CH_2PO_3R_6$, $OSO_3R_6$, $OSO_2(CH_2)_jCH_3$, $CH_2SO_3R_6$, or CN, where j is an integer from 0 to 3; wherein, $R_2$=H, $OR_6$, $OC(O)R_7$, $NO_2$, $NH_2$, $N(R_6)_2$, Cl, Br, I, F, CHO, $CO_2R_6$, $C(O)N(R_6)_2$, $C(N\sim OH)NH_2$, $OPO_3R_6$, $OPO_2(CH_2)_jCH_3$, $CH_2PO_3R_6$, $OSO_3R_6$, $OSO_2(CH_2)_jCH_3$, $CH_2SO_3R_6$, or CN, where j is an integer from 0 to 3; wherein, $R_3$=H, $OR_6$, $OC(O)R_7$, $NO_2$, $NH_2$, $N(R_6)_2$, Cl, Br, I, F, CHO, $CO_2R_6$, $C(O)N(R_6)_2$, $C(N\sim OH)NH_2$, $OPO_3R_6$, $OPO_2(CH_2)_jCH_3$, $CH_2PO_3R_6$, $OSO_3R_6$, $OSO_2(CH_2)_jCH_3$, $CH_2SO_3R_6$, or CN, where j is an integer from 0 to 3; wherein, $R_4$=H, $OR_6$, $OC(O)R_7$, $NO_2$, $NH_2$, $N(R_6)_2$, Cl, Br, I, F, CHO, $CO_2R_6$, $C(O)N(R_6)_2$, $C(N\sim OH)NH_2$, $OPO_3R_6$, $OPO_2(CH_2)_jCH_3$, $CH_2PO_3R_6$, $OSO_3R_6$, $OSO_2(CH_2)_jCH_3$, $CH_2SO_3R_6$, or CN, where j is an integer from 0 to 3; wherein, $R_5$=H or $(CH_2)_kCH_3$, where k is an integer from 0 to 4; wherein, $R_6$=H, $C(CH_3)_3$, $CH(CH_3)_2$, $CH_2CH(CH_3)_2$, $CH(CH_3)(CH_2)_mCH_3$, or $(CH_2)_mCH_3$, where m is an integer from 0 to 3; wherein, $R_7$=$R_6$, $OR_6$, or $N(R_6)_2$.

Also provided are chromogenic sialidase substrate compounds having the following formula:

General Structure IIIa

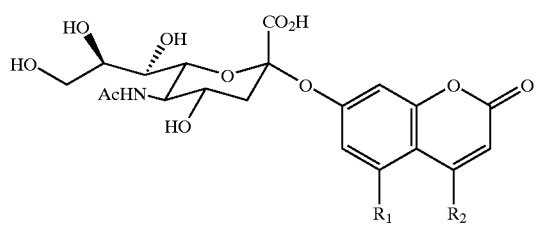

wherein, $R_1$=H, $OR_3$, $OC(O)R_4$, $NO_2$, $NH_2$, $N(R_3)_2$, Cl, Br, I, F, CHO, $CO_2R_3$, $C(O)N(R_3)_2$, $C(N\sim OH)NH_2$, $OPO_3R_3$, $OPO_2(CH_2)_jCH_3$, $CH_2PO_3R_3$, $OSO_3R_3$, $OSO_2(CH_2)_jCH_3$, $CH_2SO_3R_3$, or CN, where j is an integer from 0 to 3; wherein, $R_2$=H, $C(CH_3)_3$, $CH(CH_3)_2$, $CH_2CH(CH_3)_2$, $CH(CH_3)(CH_2)_mCH_3$, or $(CH_2)_mCH_3$, where m is an integer from 0 to 3; wherein $R_3$=H, $C(CH_3)_3$, $CH(CH_3)_2$, $CH_2CH(CH_3)_2$, $CH(CH_3)(CH_2)_mCH_3$, or $(CH_2)_mCH_3$, where m is an integer from 0 to 3; wherein, $R_4$=$R_3$, $OR_3$, or $N(R_3)_2$.

Also provided are chromogenic sialidase substrate compounds having the following formula:

General Structure IIIb

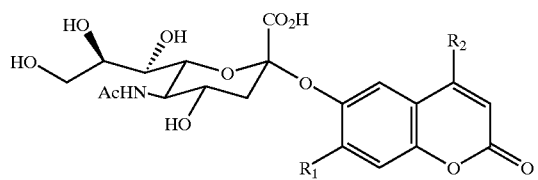

wherein, $R_1$=H, $OR_3$, $OC(O)R_4$, $NO_2$, $NH_2$, $N(R_3)_2$, Cl, Br, I, F, CHO, $CO_2R_3$, $C(O)N(R_3)_2$, $C(N\sim OH)NH_2$, $OPO_3R_3$, $OPO_2(CH_2)_jCH_3$, $CH_2PO_3R_3$, $OSO_3R_3$, $OSO_2(CH_2)_jCH_3$, $CH_2SO_3R_3$, or CN, where j is an integer from 0 to 3; wherein, $R_2$=H, $C(CH_3)_3$, $CH(CH_3)_2$, $CH_2CH(CH_3)_2$, $CH(CH_3)(CH_2)_mCH_3$, or $(CH_2)_mCH_3$, where m is an integer from 0 to 3; wherein $R_3$=H, $C(CH_3)_3$, $CH(CH_3)_2$, $CH_2CH(CH_3)_2$, $CH(CH_3)(CH_2)_mCH_3$, or $(CH_2)_mCH_3$, where m is an integer from 0 to 3; wherein, $R_4$=$R_3$, $OR_3$, or $N(R_3)_2$.

Also provided are chromogenic sialidase substrate compounds having the following formula:

General Structure IVa

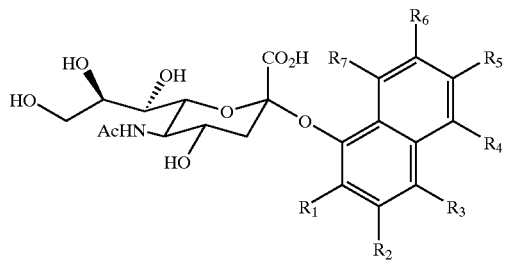

wherein, $R_1$=H, $OR_8$, $OC(O)R_9$, $NO_2$, $NH_2$, $N(R_8)_2$, Cl, Br, I, F, CHO, $CO_2R_8$, $C(O)N(R_8)_2$, $C(N\sim OH)NH_2$, $OPO_3R_8$, OPO$_2$(CH$_2$)$_j$CH$_3$, CH$_2$PO$_3$R$_8$, OSO$_3$R$_8$, OSO$_2$(CH$_2$)$_j$CH$_3$, CH$_2$SO$_3$R$_8$, or CN, where j is an integer from 0 to 3; wherein, R$_2$=H, OR$_8$, OC(O)R$_9$, NO$_2$, NH$_2$, N(R$_8$)$_2$, Cl, Br, I, F, CHO, CO$_2$R$_8$, C(O)N(R$_8$)$_2$, C(N~OH)NH$_2$, OPO$_3$R$_8$, OPO$_2$(CH$_2$)$_j$CH$_3$, CH$_2$PO$_3$R$_8$, OSO$_3$R$_8$, OSO$_2$(CH$_2$)$_j$CH$_3$, CH$_2$SO$_3$R$_8$, or CN, where j is an integer from 0 to 3; wherein, R$_3$=H, OR$_8$, OC(O)R$_9$, NO$_2$, NH$_2$, N(R$_8$)$_2$, Cl, Br, I, F, CHO, CO$_2$R$_8$, C(O)N(R$_8$)$_2$, C(N~OH)NH$_2$, OPO$_3$R$_8$, OPO$_2$(CH$_2$)$_j$CH$_3$, CH$_2$PO$_3$R$_8$, OSO$_3$R$_8$, OSO$_2$(CH$_2$)$_j$CH$_3$, CH$_2$SO$_3$R$_8$, or CN, where j is an integer from 0 to 3; wherein, R$_4$=H, OR$_8$, OC(O)R$_9$, NO$_2$, NH$_2$, N(R$_8$)$_2$, Cl, Br, I, F, CHO, CO$_2$R$_8$, C(O)N(R$_8$)$_2$, C(N~OH)NH$_2$, OPO$_3$R$_8$, OPO$_2$(CH$_2$)$_j$CH$_3$, CH$_2$PO$_3$R$_8$, OSO$_3$R$_8$, OSO$_2$(CH$_2$)$_j$CH$_3$, CH$_2$SO$_3$R$_8$, or CN, where j is an integer from 0 to 3; wherein, R$_5$=H, OR$_8$, OC(O)R$_9$, NO$_2$, NH$_2$, N(R$_8$)$_2$, Cl, Br, I, F, CHO, CO$_2$R$_8$, C(O)N(R$_8$)$_2$, C(N~OH)NH$_2$, OPO$_3$R$_8$, OPO$_2$(CH$_2$)$_j$CH$_3$, CH$_2$PO$_3$R$_8$, OSO$_3$R$_8$, OSO$_2$(CH$_2$)$_j$CH$_3$, CH$_2$SO$_3$R$_8$, or CN, where j is an integer from 0 to 3; wherein, R$_6$=H, OR$_8$, OC(O)R$_9$, NO$_2$, NH$_2$, N(R$_8$)$_2$, Cl, Br, I, F, CHO, CO$_2$R$_8$, C(O)N(R$_8$)$_2$, C(N~OH)NH$_2$, OPO$_3$R$_8$, OPO$_2$(CH$_2$)$_j$CH$_3$, CH$_2$PO$_3$R$_8$, OSO$_3$R$_8$, OSO$_2$(CH$_2$)$_j$CH$_3$, CH$_2$SO$_3$R$_8$, or CN, where j is an integer from 0 to 3; wherein, R$_7$=H, OR$_8$, OC(O)R$_9$, NO$_2$, NH$_2$, N(R$_8$)$_2$, Cl, Br, I, F, CHO, CO$_2$R$_8$, C(O)N(R$_8$)$_2$, C(N~OH)NH$_2$, OPO$_3$R$_8$, OPO$_2$(CH$_2$)$_j$CH$_3$, CH$_2$PO$_3$R$_6$, OSO$_3$R$_8$, OSO$_2$(CH$_2$)$_j$CH$_3$, CH$_2$SO$_3$R$_8$, or CN, where j is an integer from 0 to 3; wherein R$_8$=H, C(CH$_3$)$_3$, CH(CH$_3$)$_2$, CH$_2$CH(CH$_3$)$_2$, CH(CH$_3$)(CH$_2$)$_m$CH$_3$, or (CH$_2$)$_m$CH$_3$, where m is an integer from 0 to 3; wherein, R$_9$=R$_8$, OR$_8$, or N(R$_8$)$_2$.

Also provided are chromogenic sialidase substrate compounds having the following formula:

General Structure IVb

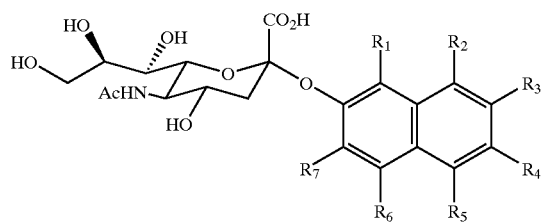

wherein, R$_1$=H, OR$_8$, OC(O)R$_9$, NO$_2$, NH$_2$, N(R$_8$)$_2$, Cl, Br, I, F, CHO, CO$_2$R$_8$, C(O)N(R$_8$)$_2$, C(N~OH)NH$_2$, OPO$_3$R$_8$, OPO$_2$(CH$_2$)$_j$CH$_3$, CH$_2$PO$_3$R$_8$, OSO$_3$R$_8$, OSO$_2$(CH$_2$)$_j$CH$_3$, CH$_2$SO$_3$R$_8$, or CN, where j is an integer from 0 to 3; wherein, R$_2$=H, OR$_8$, OC(O)R$_9$, NO$_2$, NH$_2$, N(R$_8$)$_2$, Cl, Br, I, F, CHO, CO$_2$R$_8$, C(O)N(R$_8$)$_2$, C(N~OH)NH$_2$, OPO$_3$R$_8$, OPO$_2$(CH$_2$)$_j$CH$_3$, CH$_2$PO$_3$R$_8$, OSO$_3$R$_8$, OSO$_2$(CH$_2$)$_j$CH$_3$, CH$_2$SO$_3$R$_8$, or CN, where j is an integer from 0 to 3; wherein, R$_3$=H, OR$_8$, OC(O)R$_9$, NO$_2$, NH$_2$, N(R$_8$)$_2$, Cl, Br, I, F, CHO, CO$_2$R$_8$, C(O)N(R$_8$)$_2$, C(N~OH)NH$_2$, OPO$_3$R$_8$, OPO$_2$(CH$_2$)$_j$CH$_3$, CH$_2$PO$_3$R$_8$, OSO$_3$R$_8$, OSO$_2$(CH$_2$)$_j$CH$_3$, CH$_2$SO$_3$R$_8$, or CN, where j is an integer from 0 to 3; wherein, R$_4$=H, OR$_8$, OC(O)R$_9$, NO$_2$, NH$_2$, N(R$_8$)$_2$, Cl, Br, I, F, CHO, CO$_2$R$_8$, C(O)N(R$_8$)$_2$, C(N~OH)NH$_2$, OPO$_3$R$_8$, OPO$_2$(CH$_2$)$_j$CH$_3$, CH$_2$PO$_3$R$_8$, OSO$_3$R$_8$, OSO$_2$(CH$_2$)$_j$CH$_3$, CH$_2$SO$_3$R$_8$, or CN, where j is an integer from 0 to 3; wherein, R$_5$=H, OR$_8$, OC(O)R$_9$, NO$_2$, NH$_2$, N(R$_8$)$_2$, Cl, Br, I, F, CHO, CO$_2$R$_8$, C(O)N(R$_8$)$_2$, C(N~OH)NH$_2$, OPO$_3$R$_8$, OPO$_2$(CH$_2$)$_j$CH$_3$, CH$_2$PO$_3$R$_8$, OSO$_3$R$_8$, OSO$_2$(CH$_2$)$_j$CH$_3$, CH$_2$SO$_3$R$_8$, or CN, where j is an integer from 0 to 3; wherein, R$_6$=H, OR$_8$, OC(O)R$_9$, NO$_2$, NH$_2$, N(R$_8$)$_2$, Cl, Br, I, F, CHO, CO$_2$R$_8$, C(O)N(R$_8$)$_2$, C(N~OH)NH$_2$, OPO$_3$R$_8$, OPO$_2$(CH$_2$)$_j$CH$_3$, CH$_2$PO$_3$R$_8$, OSO$_3$R$_8$, OSO$_2$(CH$_2$)$_j$CH$_3$, CH$_2$SO$_3$R$_8$, or CN, where is an integer from 0 to 3; wherein, R$_7$=H, OR$_8$, OC(O)R$_9$, NO$_2$, NH$_2$, N(R$_8$)$_2$, Cl, Br, I, F, CHO, CO$_2$R$_8$, C(O)N(R$_8$)$_2$, C(N~OH)NH$_2$, OPO$_3$R$_8$, OPO$_2$(CH$_2$)$_j$CH$_3$, CH$_2$PO$_3$R$_8$, OSO$_3$R$_8$, OSO$_2$(CH$_2$)$_j$CH$_3$, CH$_2$SO$_3$R$_8$, or CN, where j is an integer from 0 to 3; wherein, R$_8$=H, C(CH$_3$)$_3$, CH(CH$_3$)$_2$, CH$_2$CH(CH$_3$)$_2$, CH(CH$_3$)(CH$_2$)$_m$CH$_3$, or (CH$_2$)$_m$CH$_3$, where m is an integer from 0 to 3; wherein, R$_9$=R$_8$, OR$_8$, or N(R$_8$)$_2$.

The subject invention further pertains to analogs, salts, derivatives, and mixtures of the subject compounds.

Figure 1A:
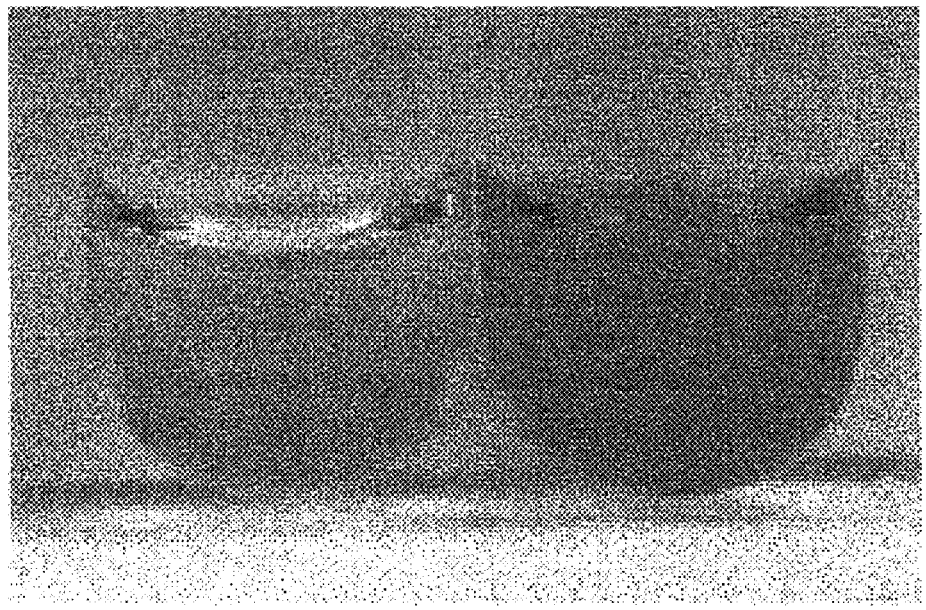
FIG. 1a. A red color change produced by the substrate compound 14 (a) no sialidase added (left), (b) with sialidase added (right).

This application contains at least one drawing executed in color. Copies of the patent issuing from this application with color drawings will be provided by the U.S. Patent Office upon request and payment of the necessary fee.

DETAILED DISCLOSURE OF THE INVENTION

The subject invention pertains to materials and methods useful for detecting sialidase. Sialidase is an enzyme known to be associated with a variety of pathological conditions.

Sialidases are produced by bacteria, viruses, and protozoa; therefore, detecting the presence of sialidase in a biological sample can be indicative of the presence of these microbes. In specific embodiments, the detection of sialidases can be performed according to the subject invention in order to identify vaginal and periodontal infections, as well as to detect *Pseudomonas aeruginosa* in cystic fibrosis patients.

The presence of sialidase is detected according to the subject invention through the use of novel chromogenic substrate compounds. These compounds advantageously provide a visible color change when acted upon by sialidase. Thus, these substrates, when utilized according to the teachings of the subject invention, can be used to easily and accurately detect the presence of sialidase in a sample. In a preferred embodiment, the sample which is tested is a biological sample such as blood, mucous, saliva, and the like.

The subject invention provides compounds having structures as shown in General Structures I, II, IIIa, IIIb, IVa, and IVb. The invention further includes derivatives, analogs, and salts of the exemplified compounds. These derivatives, analogs, and salts, which can readily be prepared by one skilled in the art and having the benefit of the instant disclosure, fall within the scope of the present invention so long as such compounds have the characteristic of producing a color change when acted upon by a sialidase enzyme.

The compounds of the subject invention can be employed in a wide variety of assay formats. Typically, the assay will involve contacting a sample to be tested for the presence of sialidase with a chromogenic enzyme substrate of the subject invention. A color change occurring after the sample is contacted with the substrate is indicative of the presence of sialidase. The assay may optionally utilize positive and/or negative controls to aid in the interpretation and verification of the results. The results may also be quantified using standard optical measuring instrumentation.

Materials and Methods

Biochemical Evaluation for the Chromogenic Product of Sialidase Substrate Compounds. Sialidase can be obtained from, for example, purified recombinant bacterial sialidase from Salmonella T., whole influenza virus, or culture medium containing secreted human sialidase from 2CFSME0 cell line. The sialidase preparation is added to a buffer of 0.1 M sodium acetate at pH6.0, and the substrate compound is provided at about 0.5 mM concentration. The reaction takes place in room temperature for 20 mins in a volume of 100 µl. At the end of the reaction, the pH is adjusted by adding a solution (0.2 M glycine, and sodium hydroxide with a pH value of 11.0). A color change is readily visible as exemplified by FIGS 1a and 1b. The color change can be quantitated by measuring the light absorption of the reaction mixture.

Figure 1B:
FIG. 1b. An orange color change produced by the substrate compound 11 (a) no sialidase added (left), (b) with sialidase added (right).

FIG. 1a shows a red color change produced by the substrate compound 14 (a) no sialidase added (left), (b) with sialidase added (right). FIG. 1b shows an orange color change produced by the substrate compound 11 (a) no sialidase added (left), (b) with sialidase added (right).

General Methodologies. The following general methods are applicable to the synthesis of compounds of the invention. Modifications or variations of these methods can readily be utilized by those skilled in the art having the benefit of the instant disclosure.

Esterification. N-Acetyl-D-neuraminic acid is treated with methanol-washed Dowex 50W-X4 in methanol with stirring at room temperature for a period of time, generally 4 h. The mixture is filtered, and the filtrate is concentrated to give the desired esterified product after crystallization.

Those skilled in the art would recognize that other standard procedures are available for esterification of the same material, such as the use of other cation exchange resins, e.g., Amberlyst 15 or Dowex 50W-X8, among others.

O-Acetylation and Glycosyl Chloride Preparation. Treatment of the esterified product with acetyl chloride with stirring at room temperature under anhydrous conditions for a period of time, generally 20–24 h, results in formation of the per-O-acetylated glycosyl chloride. Note that in some instances the bubbling of dry hydrogen chloride (gas) into the reaction vessel is necessary to effect glycosyl chloride formation. Concentration of the reaction mixture with the water bath temperature not exceeding 35° C., and drying the residue in vacuo provides the product as a foam sufficiently pure for subsequent reactions.

Those skilled in the art would recognize that other standard procedures are available for O-acetylation and glycosyl chloride preparation of the same material, including a previously reported two-step procedure (Kuhn, et al., 1966) which involves per-O-acetylation of the same material with acetic anhydride in perchloric acid, followed by formation of the glycosyl chloride by treatment with acetyl chloride.

O-Glycosylation. Treatment of the substituted hydroxybenzaldehyde derivative with sodium hydride in tetrahydrofuran with stirring at room temperature for a period of time, generally 1–3 h, results in formation of the sodium salt. Subsequent treatment of the sodium salt with the glycosyl chloride (compound 3) with stirring, for a period of time, generally 12–60 h, at room temperature results in O-glycosylation. Concentration of the reaction mixture, treatment of the residue with ethyl acetate and water, separation and drying of the organic phase, concentration of the organic phase, and column chromatography of the crude material affords the desired O-glycoside.

Those skilled in the art would recognize that other standard procedures are available for O-glycosylation of the same materials, such as traditional Lewis Acid-mediated O-glycosylation methodologies (Okamoto and Goto, 1990), as well as the use of alternate salts of the substituted aromatic hydroxyl derivative, including tetrabutylammonium (Baggett and Marsden, 1982) or silver (Holmquist and Brossmer, 1972) salts, among others.

De-O-acetylation and De-esterification. The protected O-glycoside is taken up in aqueous sodium hydroxide and stirred at room temperature for a period of time, generally 1–4 h. The mixture is then adjusted to pH 3–5 with Dowex 50W-X4 (H+) resin. Filtration, followed by lyophilization of the filtrate affords the desired de-O-acetylated and de-esterified material.

Those skilled in the art would recognize that other standard procedures are available for the complete de-O-acetylation and de-esterification of the same material, including a two-step procedure which involves complete de-O-acetylation of the same material with sodium methoxide in methanol or with an appropriate ion exchange resin, e.g. Amberlite IRA-400 (OH–), followed by de-esterification using conditions of acid hydrolysis or base hydrolysis.

Synthesis of Chromogenic Substrates of Sialidases

A. Compounds with General Structure I and their salts and derivatives, may be prepared using any of several methods known in the art for the synthesis of substituted sialic acid analogs containing analogous structures.

To illustrate, synthetic approaches for selected examples (FIG. 2) from General Structure I are summarized in the following reaction scheme and are representative of the types of procedures which can be employed. Table 1 lists specific compounds, the synthesis of which is exemplified herein.

TABLE 1

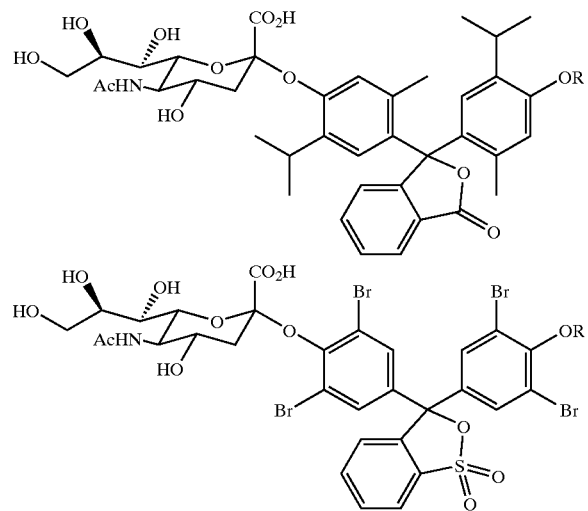

| Compound | $R_1$ | $R_2$ | $R_3$ |
|---|---|---|---|
| 5 | H | H | CHO |
| 6 | H | H | CH=CHNO$_2$ |
| 10 | H | OCH$_3$ | CHO |
| 11 | H | OCH$_3$ | CH=CHNO$_2$ |
| 13 | OCH$_3$ | H | CHO |
| 14 | OCH$_3$ | H | CH=CHNO$_2$ |

In another specific embodiment, the subject invention includes compounds having the following structures:

Advantageously, these compounds produce a blue color change when acted upon by a sialidase.

Figure 2:
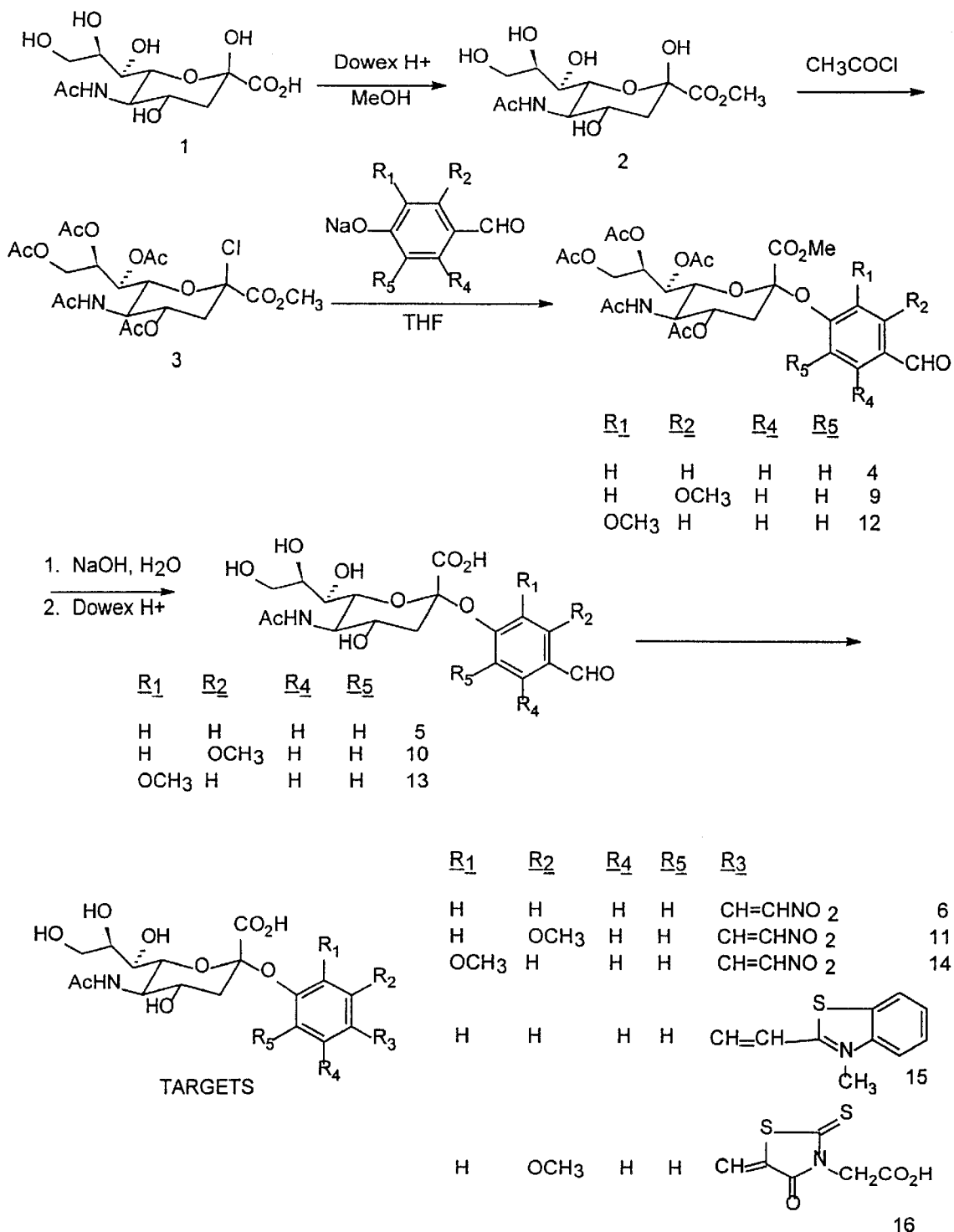
FIG. 2—synthetic approaches for selected examples from General Structure I are summarized in this reaction scheme.

FIG. 2 illustrates constructing a basic skeleton of General Structure I via acid-mediated esterification of commercially available N-acetyl-D-neuraminic acid (1) to provide methyl N-acetyl-D-neuraminate (2), and subsequent per-O-acetylation and generation of the glycosyl chloride (3) according to modifications of known procedures (Kuhn et al., 1966; Ogura et al., 1986; Patel and Richardson, 1986). Treatment of compound 3 with the sodium salt of numerous substituted hydroxybenzaldehyde derivatives would provide the key intermediates to the desired targets (compounds 4, 9, and 12). Generation of the sodium salt would be accomplished with sodium hydride in tetrahydrofuran. This method of O-glycosylation has already been applied in the stereoselective preparation of numerous -O-glycosides of N-acetyl-D-neuraminic acid (Myers, et al., 1980; Eschenfelder and Brossmer, Carbohydr. Res., 1987; Eschenfelder and Brossmer, Glycoconjugate J., 1987; Okamoto and Goto, 1990; Warner and O'Brien, 1979) derived from aromatic hydroxyls. However, none of the products described herein are contained in the aforementioned references. Synthetic approaches to or references to synthetic approaches to intermediates (1) and (2) are contained in the aforementioned references. Subsequent de-O-acetylation and de-esterification of the resulting intermediates can be accomplished with an aqueous sodium hydroxide solution and workup involving acidification of the reaction medium. This provides access to the formyl substituted phenolic-O-glycosides (compounds 5, 10, and 13).

Treatment of the derived targets (compounds 5, 10, and 13) with nitromethane, ammonium acetate, and acetic acid in ethanol under reflux provides access to the desired nitrovinyl targets (compounds 6, 11, and 14). This procedure has been utilized in the preparation of nitrovinyl analogs of other monosaccharides (Patel and Richardson, 1986; Aamlid, et al., 1990) as chromogenic substrates for the assay of glycosidases; however, none of the products or intermediates described herein are contained in the aforementioned references.

It should also be noted that the p-nitrophenyl O-glycoside of N-acetylneuraminic acid (General Structure I, wherein, $R_1=R_2=R_4=R_5=H$ and $R_3=NO_2$ has been reported as a chromogenic substrate of sialidases (Eschenfelder and Brossmer, Carbohydr. Res., 1987). Condensation of compounds 5, 10, or 13 with any of numerous aromatic keto compounds in the presence of ammonia and ammonium chloride, provides ready access to numerous chromogenic substrates of sialidases (for representative examples, see compounds 15 and 16 FIG. 2) of General Structure I.

B. Compounds with General Structure II and their salts and derivatives, may be prepared using any of several methods known in the art for the synthesis of substituted sialic acid analogs containing analogous structures.

Figure 3:
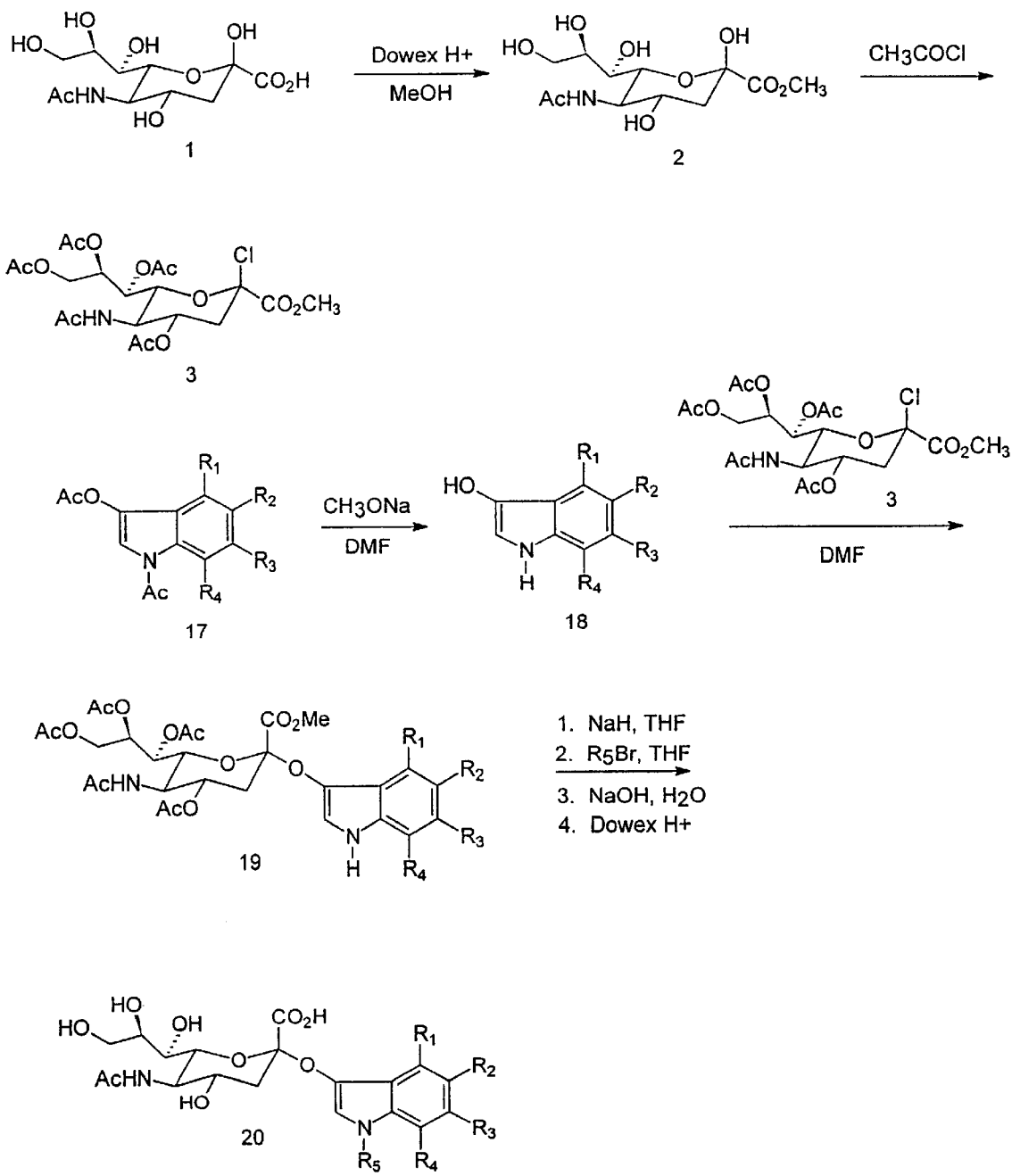
FIG. 3—synthetic approaches for selected examples from General Structure II are summarized in this reaction scheme.

To illustrate, synthetic approaches for selected examples from General Structure II (FIG. 3) are summarized in the following reaction scheme and are representative of the types of procedures to be employed. FIG. 3 illustrates constructing a basic skeleton of General Structure II via acid-mediated esterification of commercially available N-acetyl-D-neuraminic acid (1) to provide methyl N-acetyl-D-neuraminate (2), and subsequent per-O-acetylation and generation of the glycosyl chloride (3) according to modifications of known procedures (Kuhn et al., 1966; Ogura et al., 1986; Patel and Richardson, 1986). Treatment of any of numerous substituted indoxyl 1,3-diacetate compounds (compound 17) with sodium methoxide in anhydrous N,N-dimethylformamide readily provides the modified 3-hydroxy indole (compound 18). This procedure has been utilized in the preparation of 5-bromo-3-hydroxyindole (compound 18, wherein, $R_1=R_3=R_4=H$ and $R_2=Br$) (Eschenfelder and Brossmer, Glycoconjugate J., 1987). Subsequent treatment of the compound 18 with compound 3 in anhydrous N,N-dimethylformamide provides the desired modified indole O-glycoside (compound 19) according to a known procedure for the preparation of methyl N-acetyl-4,7,8,9-tetra-O-acetyl-2-O-(5-bromoindol-3-yl)-α-D-neuraminate (compound 19, wherein, $R_1=R_3=R_4=R_5=H$ and $R_2=Br$) (Eschenfelder and Brossmer, Glycoconjugate J., 1987). Analogously, 3-indolyl O-glycosides of other monosaccharides have been prepared using these and alternate conditions (Robertson, 1927; Freudenberg, et al., 1952; Anderson and Leeback, 1961; Horwitz, et al., 1964; Ley, et al., 1987); however, none of the products or intermediates described herein are contained in the aforementioned references. Treatment of compound 19 with sodium hydride in tetrahydrofuran, followed with an alkyl halide ($R_5Br$) would provide the N-alkylated product. Subsequent de-O-acetylation and de-esterification of the resulting intermediates can be accomplished with an aqueous sodium hydroxide solution and workup involving acidification of the reaction medium. This provides access to the substituted indole - O-glycosides (compound 20). It should be noted that N-acetyl-2-O-(5-bromoindol-3-yl)-α-D-neuraminic acid (compound 20, wherein, $R_1=R_3=R_4=R_5=H$ and $R_2=Br$) has been utilized as a chromogenic substrate for sialidases of many different origins (Eschenfelder and Brossmer, *Glycoconjugate J.*, 1987).

C. Compounds with General Structures IIIa and IIIb and their salts and derivatives, may be prepared using any of several methods known in the art for the synthesis of substituted sialic acid analogs containing analogous structures.

Figure 4:
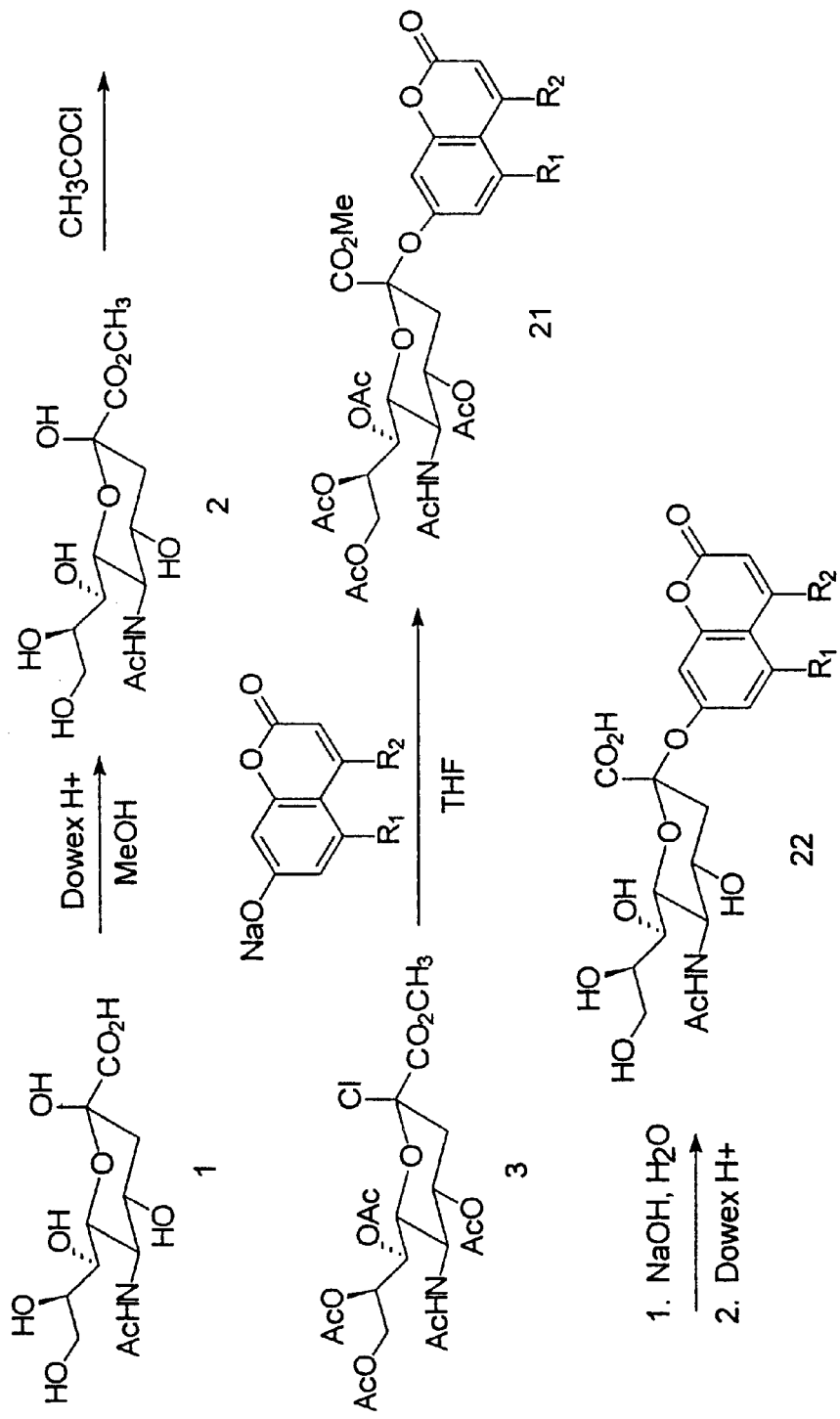
FIG. 4—synthetic approaches for selected examples from General Structures IIIa and IIIb are summarized in this reaction scheme.

To illustrate, synthetic approaches for selected examples from General Structures IIIa and IIIb are summarized in FIG. 4 and are representative of the types of procedures to be employed. FIG. 4 illustrates constructing a basic skeleton of General Structures IIIa/IIIb via acid-mediated esterification of commercially available N-acetyl-D-neuraminic acid (1) to provide methyl N-acetyl-D-neuraminate (2), and subsequent per-O-acetylation and generation of the glycosyl chloride (3) according to modifications of known procedures (Kuhn et al., 1966; Ogura et al., 1986; Patel and Richardson, 1986). Treatment of compound (3) with the sodium salt of numerous substituted coumarin derivatives provides the key intermediates to the desired targets (compound 21). Generation of the sodium salt can be accomplished with sodium hydride in tetrahydrofuran. This method of O-glycosylation has already been applied in the stereoselective preparation of numerous -O-glycosides on N-acetyl-D-neuraminic acid (Myers, et al., 1980; Eschenfelder and Brossmer, *Carbohydr. Res.*, 1987; Eschenfelder and Brossmer, *Glycoconjugate* ., 1987; Okamoto and Goto, 1990; Warner and O'Brien, 1979) derived from aromatic hydroxyls, including specific examples for the preparation of a substituted coumarin O-glycoside (compound 21, wherein, $R_1=H$ and $R_2=CH_3$) (Warner and O'Brien, 1979; Myers, et al., 1980). Subsequent de-O-acetylation and de-esterification of the resulting intermediates can be accomplished with an aqueous sodium hydroxide solution and workup involving acidification of the reaction medium. This provides access to the modified coumarin O-glycosides (compound 22).

D. Compounds with General Structures IVa and IVb and their salts and derivatives, may be prepared using any of several methods known in the art for the synthesis of substituted sialic acid analogs containing analogous structures.

Figure 5:
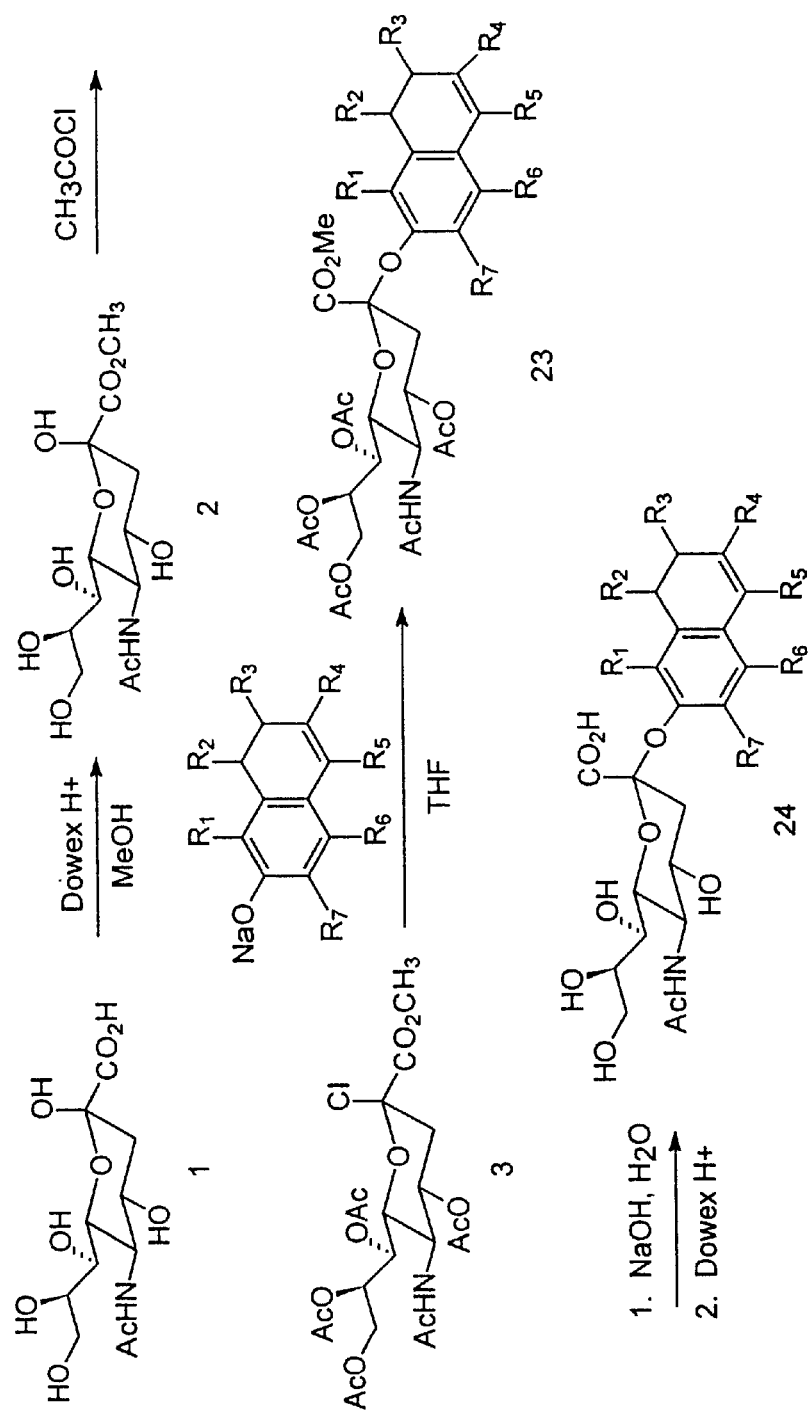
FIG. 5—synthetic approaches for selected examples from General Structures IVa and IVb are summarized in this reaction scheme.

To illustrate, potential synthetic approaches for selected examples from General Structures IVa and IVb are summarized in FIG. 5 and are representative of the types of procedures which can be employed. FIG. 5 illustrates constructing a basic skeleton of General Structure IVa/IVb via acid-mediated esterification of commercially available N-acetyl-D-neuraminic acid (1) to provide methyl N-acetyl-D-neuraminate (2), and subsequent per-O-acetylation and generation of the glycosyl chloride (3) according to modifications of known procedures (Kuhn et al., 1966; Ogura et al., 1986; Patel and Richardson, 1986). Treatment of compound (3) with the sodium salt of numerous substituted naphthol derivatives would provide the key intermediates to the desired targets (compound 23). Generation of the sodium salt can be accomplished with sodium hydride in tetrahydrofuran. This method of O-glycosylation has already been applied in the stereoselective preparation of numerous -O-glycosides on N-acetyl-D-neuraminic acid (Myers, et al., 1980; Eschenfelder and Brossmer, *Carbohydr. Res.*, 1987; Eschenfelder and Brossmer, *Glycoconjugate J.*, 1987; Okamoto and Goto, 1990; Warner and O'Brien, 1979) derived from aromatic hydroxyls. However, none of the products described herein are contained in the aforementioned references. Synthetic approaches to, or references to synthetic approaches to, intermediates (1) and (2) are contained in the afornentioned references. Subsequent de-O-acetylation and de-esterification of the resulting intermediates can be accomplished with an aqueous sodium hydroxide solution and workup involving acidification of the reaction medium. This would provide access to the modified naphthyl O-glycosides (compounds 24).

F. Biochemical Evaluation for the Chromogenic Product of the Sialidase Substrate Compound. The source of sialidase was from purified recombinant bacterial sialidase from Salmonella T., whole influenza virus, or culture medium containing secreted human sialidase from 2CFSME0 cell line. The sialidase preparation was added to a buffer of 0.1 M sodium acetate at pH6.0, and the substrate compound 14 was provided at about 0.5 mM concentration. The reaction took place in room temperature for 20 mins in a volume of 100 µl. At the end of the reaction, the pH was adjusted by adding a solution (0.2 M glycine, and sodium hydroside with a pH value of 11.0). A color change to red was readily visible as examplified by FIGS. 1a and 1b. The color change was quantitated by measuring the light absorption of the reaction mixture. The light absorption was scanned with a photospectrometer. The peak value for compound IBX4010 is 495 nm. At a substrate concentration of 0.2 mM, the light absorption at 495 nm with a 1 cm path is 1.203. The control in which the reaction mixture was kept under the same condition for 10 minutes without addition of any enzyme had an absorption of 0.282 at 495 nm with a 1 cm path.

Compound 11 was tested by the same method. At the end of the reaction with pH adjusment, a color change to orange was readily visible as exemplified by FIGS. 1a and 1b. The color change was quantitated by measuring the light absorption of the reaction mixture. Ten minutes after the reaction, the mixture of the reaction product was adjusted to basic pH and the light absorption was scanned with a photospectrometer. The peak value for compound IEBX4023 is 480 nm. At a substrate concentration of 0.2 mM, the light absorption at 480 nm with a 1 cm path is 4.065. The control in which the reaction mixture was kept under the same condition for 10 minutes without addition of any enzyme had an absorption of 1.452 at 480 nm with a 1 cm path.

G. Classes of Chromogenic Substrate Compounds of Sialidases. As used herein, the "effective amount" of a compound of the invention required for the use in the method presented herein will differ not only with the particular compound to be selected but also with the mode of application, and the nature of the sample specimen. The exact amount will be evaluated by testing with a sufficient number of clinical samples in each application as conducted by persons skilled in the art. However, a generally suitable concentration will range from about 0.1 to about 10 mM/ml of testing solutions. Furthermore, the compounds may be used as pure chemical applied to a test solution, or as a pure chemically acceptable salt or derivative. However, it is preferable to provide the active chemical or its chemically acceptable salt or derivative, as a medicinal formulation, either as a dry material (reaction solution provided seperately), or as a solution or suspension (an aqueous solution or other chemically acceptable solvent solutions), or as a dip stick. The subject specimen can be applied to the test for measuring the activity levels of sialidases. Those skilled in the art having the benefit of the instant disclosure will appreciate that amounts and modes of application are readily determinable without undue experimentation.

The following detailed examples for methods of preparation are for illustration only, and are not intended to represent a limitation of the invention. The structures of the compounds whose preparations are described below are summarized in Table 1 for modified phenol derivatives and in FIG. 3 (for a single example where $R_1$=Cl; $R_2$=Br; $R_3$=$R_4$=$R_5$=H). In all cases synthetic intermediates and products were found to be pure according to standards known to those skilled in the art (such as thin layer chromatography, melting or boiling points, gas chromatography, ion exchange chromatography, and/or high pressure liquid chromatography, elemental analysis, and spectroscopic methods). Furthermore, structures were characterized and assigned by spectroscopic methods considered standard practices by those skilled in the art (such as infrared, ultraviolet, and mass spectroscopies, $^1$H and $^{13}$C nuclear magnetic resonance spectroscopy, and/or x-ray crystallography). Selected spectral data are described for intermediates and products.

EXAMPLE 1

Preparations of Methyl N-acetyl-β-D-neuraminate (2), Methyl N-acetyl-4,7,8,9-tetra-O-acetyl-2-chloro-2-deoxy-D-neuraminate (3), Methyl N-acetyl-4,7,8,9-tetra-O-acetyl-2-O-(4-formylphenyl)-α-D-neuraminate (4), and N-acetyl-2-O-(4-formylphenyl)-α-D-neuraminic Acid (5)

Figure 6:
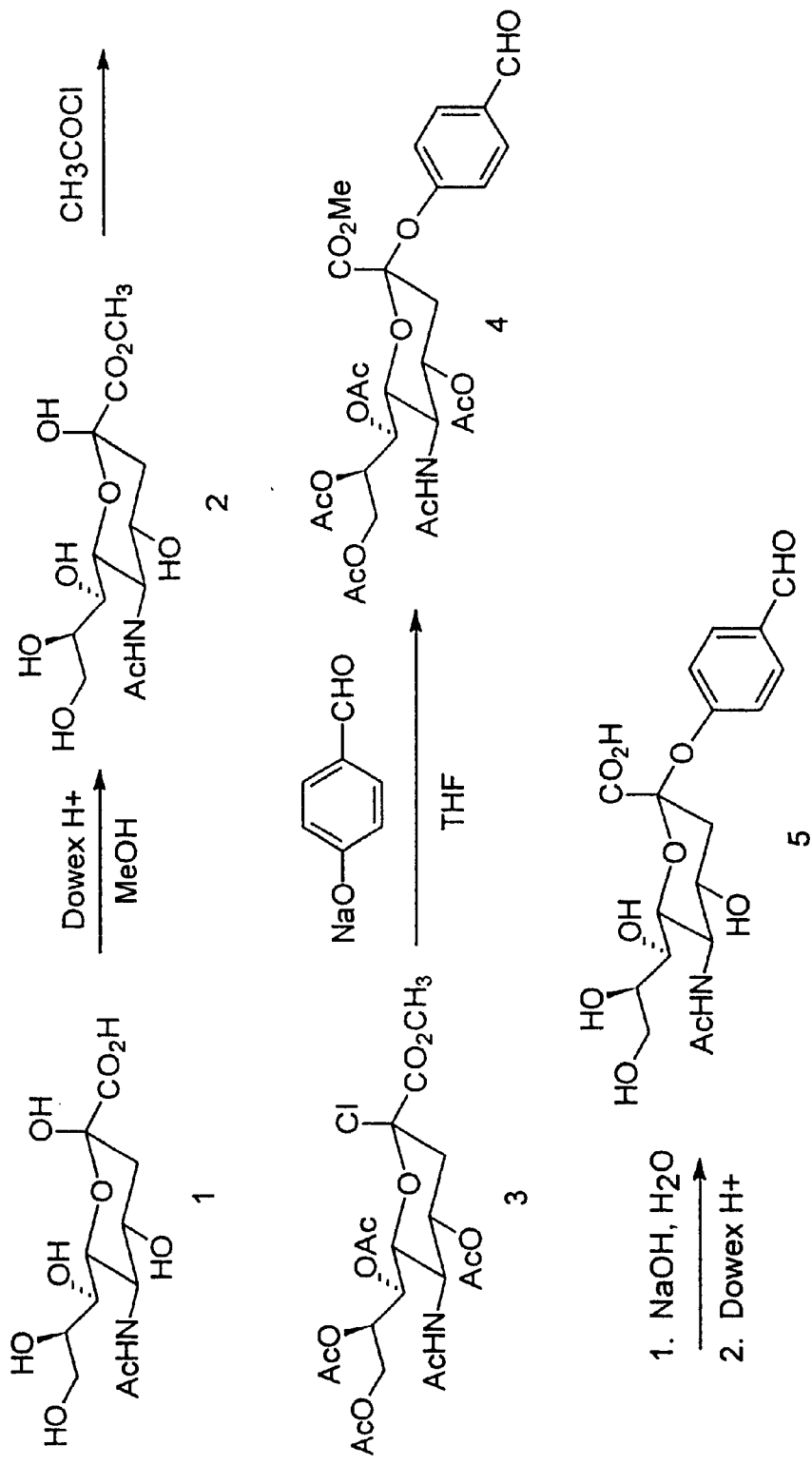
FIG. 6—shows an overall scheme for the preparation of methyl N-acetyl-β-D-neuraminate (2), methyl N-acetyl-4,7,8,9-tetra-O-acetyl-2-chloro-2-deoxy-D-neuraminate (3), methyl N-acetyl-4,7,8,9-tetra-O-acetyl-2-O-(4-formylphenyl)-α-D-neuraminate (4), and N-acetyl-2-O-(4-formylphenyl)-β-D-neuraminic acid (5).

The overall scheme is shown in FIG. 6.

Preparation of Methyl N-acetyl-β-D-neuraminate (2). To a stirred suspension of N-acetylneuraminic acid (1) (10.0 g, 32.3 mmol) in methanol (1.0 L) was added methanol-washed Dowex 50W-X4 (25.0 g) under a nitrogen atmosphere at room temperature protected from light. The resulting mixture was allowed to stir at room temperature for 4 h. The mixture was filtered and the filtrate was concentrated to dryness. The residue was crystallized from methanol to afford pure compound (2) (10.1 g, 96%): mp 178–180° C. (d). A literature reference (Kuhn et al., 1966) reports mp 179–180° C. A second literature reference (Ogura et al., 1986) reports mp 180–182° C.

$^1$H NMR (D$_2$O): (1.73 (dd, 1H, J$_{3a,4}$ 12.0 Hz, J$_{3a,3e}$ 13.3 Hz, H-3a), 1.87 (s, 3H, NAc), 2.14 (dd, 1H, J$_{3e,4}$ 5.0 Hz, H-3e), 3.33–3.48 (m, 2H), 3.52–3.58 (m, 1H), 3.62–3.68 (m, 1H), 3.65 (s, 3H, CO$_2$CH$_3$), 3.69–3.76 (m, 1H), 3.84–3.92 (m, 2H).

Preparation of Methyl N-acetyl-4,7,8,9-tetra-O-acetyl-2-chloro-2-deoxy-D-neuraminate (3). A suspension of compound (2) (3.67 g, 11.3 mmol) in acetyl chloride (225 mL) was stirred under anhydrous conditions at room temperature protected from light for 24 h. The resulting solution was concentrated to dryness, the residue was coevaporated with anhydrous ether (2×50 mL), followed by coevaporations with anhydrous benzene (2×50 mL). Note. that in all evaporations, the water bath temperature was maintained at or below 35° C. The residue was dried in vacuo to afford pure compound (3) (4.8 g, 83%) as a syrup. A literature reference (Ogura et al., 1986) reports mp 116–118° C.; whereas, a second literature reference (Kuhn et al., 1966) reports compound (3) as a syrup.

$^1$H NMR (CDCl$_3$): (1.92 (s, 3H, NAc), 2.06, 2.07, 2.10, 2.14 (4 s, 12H, 4×OAc), 2.28 (dd, 1H, J$_{3a,4}$ 11.3 Hz, J$_{3a,3e}$ 13.5 Hz, H-3a), 2.79 (dd, 1H, J$_{3e,4}$ 4.5 Hz, H-3e), 3.89 (s, 3H, CO$_2$CH$_3$), 4.07 (dd, 1H, J$_{8,9'}$ 5.6 Hz, J$_{9',9''}$ 11.6 Hz, H-9'), 4.13–4.28 (m, 1H, H-5), 4.36 (dd, 1H, J$_{6,7}$ 2.5 Hz, J$_{5,6}$ 10.5 Hz, H-6), 4.43 (dd, 1H, J$_{8,9''}$ 2.9 Hz, H-9''), 5.18 (ddd, 1H, J$_{7,8}$ 6.7 Hz, H-8), 5.40 (ddd, 1H, J$_{4,5}$ 10.4 Hz, H-4), 5.49–5.52 (m, 2H, H-7, NH).

Preparation of Methyl N-acetyl-4,7,8,9-tetra-O-acetyl-2-O-(4-formylphenyl)-α-D-neuraminate (4). To a stirred solution of 4-hydroxybenzaldehyde (121 mg, 0.98 mmol) in anhydrous tetrahydrofuran (6.0 mL) was added portionwise sodium hydride (48 mg of a 60% dispersion in mineral oil, 1.2 mmol) under a nitrogen atmosphere at room temperature. The resulting mixture was allowed to stir at room temperature for 25 min. The mixture was treated with compound (3) (500 mg, 0.98 mmol) and the resulting mixture was stirred under a nitrogen atmosphere at room temperature for 52 h. The mixture was concentrated to dryness, the residue was diluted with ethyl acetate (15 mL), and washed with water (15 mL). The aqueous phase was extracted with ethyl acetate (3×15 mL), and combined organic phases were dried with magnesium sulfate, filtered, and the filtrate was concentrated to dryness. The residue was chromatographed (silica gel, 1:1 acetone-hexanes as eluting solvent) to afford pure compound (4) (238 mg, 41%): R$_f$=0.26 (1:1 acetone-hexanes; UV, H$_2$SO$_4$).

$^1$H NMR (CDCl$_3$): (1.95 (s, 3H, NAc), 2.07, 2.09, 2.13, 2.22 (4 s, 12H, 4×OAc), 2.32 (ut, 1H, J$_{3a,3e}$=J$_{3a,4}$=13.2 Hz, H-3a), 2.77 (dd, 1H, J$_{3e,4}$ 5.0 Hz, H-3a), 3.67 (s, 3H, CO$_2$CH$_3$), 4.10–4.22 (m, 2H), 4.24–4.32 (m, 1H), 4.63 (dd, 1H, J 2.0 Hz, J 11.7 Hz), 4.97–5.06 (m, 1H), 5.30 (d, 1H, J 12.6 Hz), 5.41 (s, 2H), 7.20 (d, 2H, J 9.6 Hz, 2×ArH), 7.86 (d, 2H, J 9.6 Hz, 2×ArH), 9.95 (s, 1H, CHO).

Preparation of N-Acetyl-2-O-(4-formylphenyl)-α-D-neuraminic acid (5). A solution of compound (4) (171 mg, 0.29 mmol) in aqueous sodium hydroxide (5.0 mL of a 1.0 M solution, 5.0 mmol) was stirred at room temperature for 2 h. The resulting mixture was cooled to 0° C. and treated with methanol-washed Dowex 50W-X4 til pH 3. The mixture was filtered, the filtered resin was rinsed with water, and the filtrate was lyophilized to afford compound (5) (118 mg, 99%): R$_f$=0.31 (5:2:1 ethyl acetate-methanol-0.02% aqueous calcium chloride; UV, H$_2$SO$_4$).

$^1$H NMR (D$_2$O): (2.08 (s, 3H, NAc), 2.05–2.12 (m, 1H, H-3a), 2.84 (dd, 1H, J$_{3e,4}$ 5.6 Hz, J$_{3a,3e}$ 13.1 Hz, H-3e), 3.58–3.69 (m, 2H), 3.82–3.90 (m, 3H), 3.92–4.10 (m, 1H), 4.21 (dd, 1H, J 1.9 Hz, J 11.3 Hz), 7.32 (d, 2H, J 9.6 Hz, 2×ArH), 7.92 (d, 2H, J 9.6 Hz, 2×ArH), 9.84 (s, 1H, CHO).

EXAMPLE 2

Preparation of N-acetyl-2-O-[4-(2-nitrovinyl) phenyl]-α-D-neuraminic Acid

Figure 7:
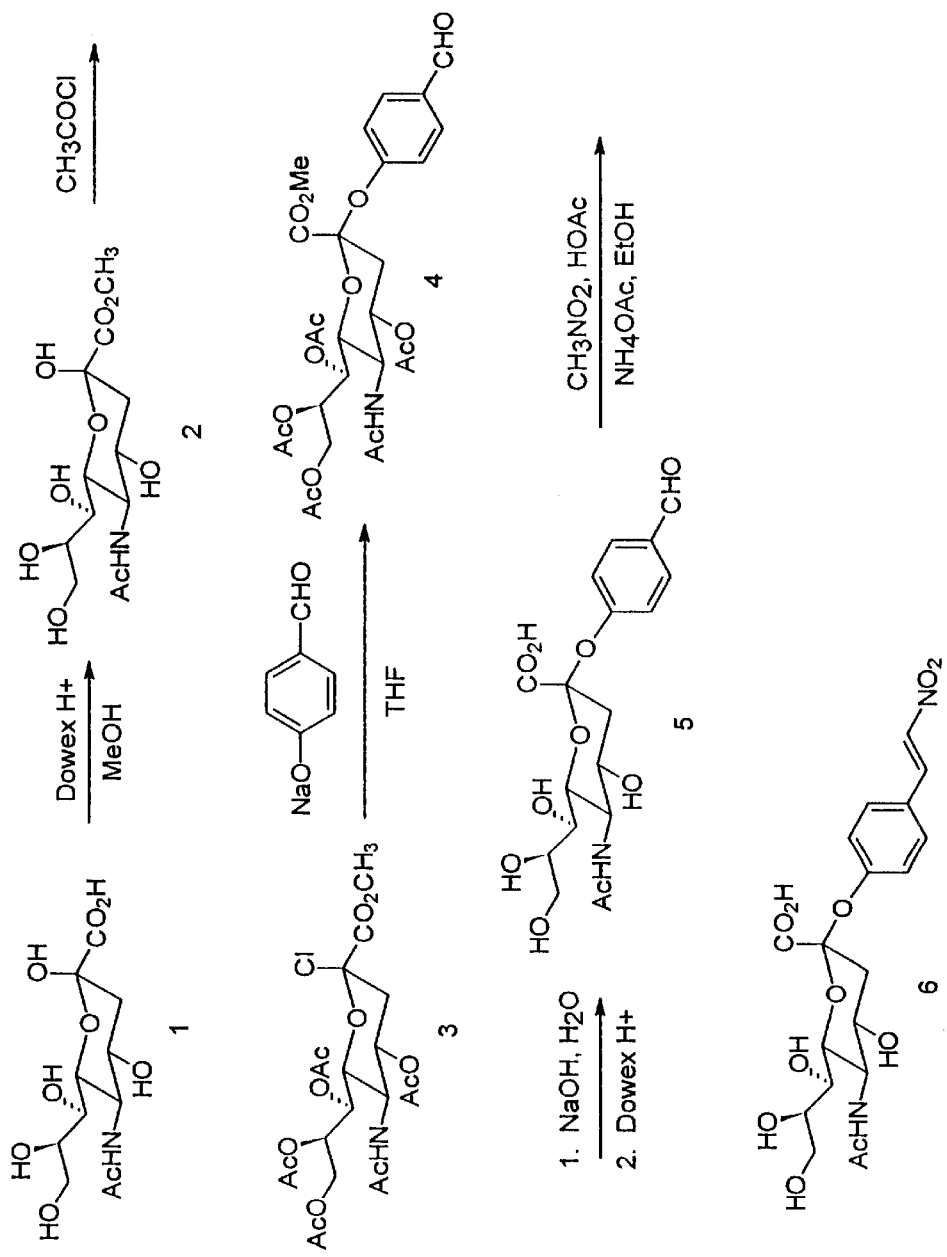
FIG. 7—shows an overall scheme for the preparation of N-acetyl-2-O-[4-(2-nitrovinyl)phenyl]-α-D-neuraminic acid (6).

The overall reaction scheme is shown in FIG. 7. For the preparations of methyl N-acetyl-β-D-neuraminate (2), methyl N-acetyl-4,7,8,9-tetra-O-acetyl-2-chloro-2-deoxy-D-neuraminate (3), methyl N-acetyl-4,7,8,9-tetra-O-acetyl-2-O-(4-formylphenyl)-α-D-neuraminate (4), and N-acetyl-2-O-(4-formylphenyl)-α-D-neuraminic acid (5), see the experimental details for Example 1.

To a stirred solution of compound (5) (50 mg, 0.10 mmol) in a mixture of ethanol (2.0 mL) and acetic acid (0.05 mL) was added ammonium acetate (50 mg, 0.65 mmol) and nitromethane (0.20 mL, 3.70 mmol) at room temperature.

The reaction mixture was heated under reflux for 30 min, cooled to room temperature, and evaporated to dryness. The residue was chromatographed (silica gel, 5:2:1 ethyl acetate-methanol-0.02% aqueous calcium chloride as eluting solvent) to afford pure compound (6) (32 mg, 68%): $R_f$=0.50 (5:2:1 ethyl acetate-methanol-0.02% aqueous calcium chloride; UV, $H_2SO_4$).

$^1$H NMR ($D_2O$): (2.05 (s, 3H, NAc), 1.95–2.02 (m, 1H, H-3a), 2.89 (dd, 1H, $J_{3e,4}$ 5.2 Hz, $J_{3a,3e}$ 12.9 Hz, H-3e), 3.57–3.69 (m, 2H), 3.85–4.00 (m, 4H), 4.06 (dd, 1H, J 1.5 Hz, J 10.5 Hz), 7.22 (d, 2H, J 9.0 Hz, 2×ArH), 7.64 (d, 2H, J 9.0 Hz, 2×ArH) 7.83 (d, 1H, J 13.5 Hz, H-vinylic), 8.13 (d, 1H, J 13.5 Hz, H-vinylic).

EXAMPLE 3

Preparation of 4-Hydroxy-2-methoxybenzaldehyde (8), Methyl N-acetyl-4,7,8,9-tetra-O-acetyl-2-O-(4-formyl-3-methoxyphenyl)-α-D-neuraminate (9) and N-acetyl-2-O-(4-formyl-3-methoxyphenyl)-α-D-neuraminic acid (10)

Figure 8:
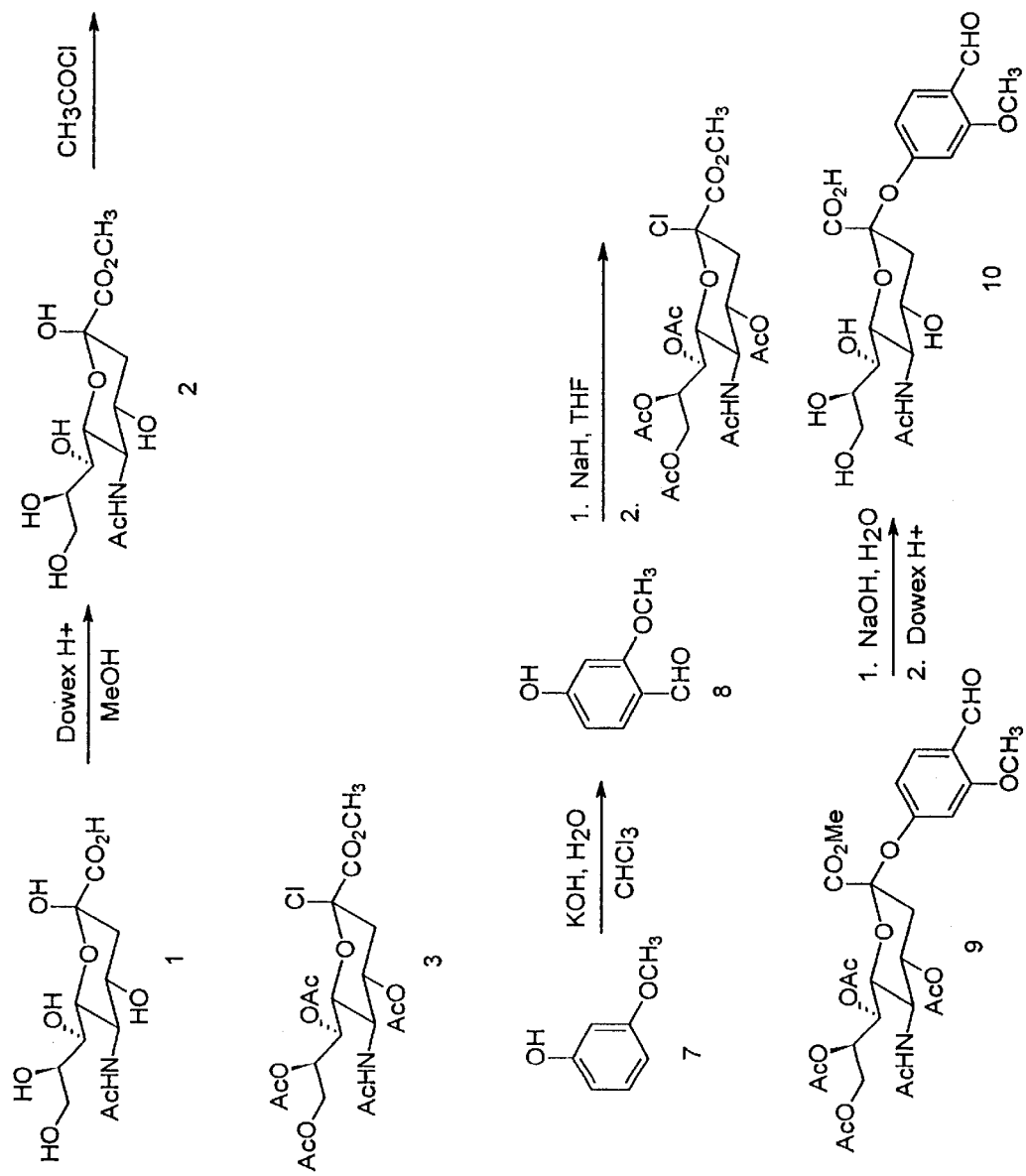
FIG. 8—shows an overall scheme for the preparation of 4-hydroxy-2-methoxybenzaldehyde (8), methyl N-acetyl-4,7,8,9-tetra-O-acetyl-2-O-(4-formyl-3-methoxyphenyl)-α-D-neuraminate (9), and N-acetyl-2-O-(4-formyl-3-methoxyphenyl)-α-D-neuraminic acid (10).

The overall reaction scheme is shown in FIG. 8.

For the preparation of methyl N-acetyl-α-D-neuraminate (2), methyl N-acetyl-4,7,8,9-tetra-O-acetyl-2-chloro-2-deoxy-D-neuraminate (3), see the experimental details presented previously.

Preparation of 4-Hydroxy-2-methoxybenzaldehyde (8). To a stirred solution of 3-methoxyphenol (14.9 g, 120 mmol) in 15% aqueous potassium hydroxide (500 mL) was added chloroform (100 mL). The resulting solution was heated under reflux for 4 h, cooled to room temperature, and treated with 10% aqueous hydrochloric acid til pH 4. The suspension was filtered, and the filter cake was rinsed with chloroform (150 mL). The chloroform phase was separated, the aqueous phase was extracted with additional portions of chloroform (3×50 mL), and the combined organic phases were dried with magnesium sulfate. The solution was then filtered through a short column (silica gel, chloroform as eluting solvent) to afford compound (8). Crystallization from ethyl acetate gave pure compound (8) (1.8 g, 10%): mp 150–152° C. A literature reference (Patel and Richardson, 1986) reports mp 154–156° C. Additional references (Tiemann and Koppe, 1881; de Kiewiet and Stephen, 1931) report mp 153° C.

$^1$H NMR ($CDCl_3$): (3.87 (s, 3H, $OCH_3$), 6.32–6.48 (m, 2H, 2×ArH), 7.62 (d, 1H, J 9.6 Hz, ArH), 10.1 (s, 1H, CHO).

Preparation of Methyl N-acetyl-4.7.8.9-tetra-O-acetyl-2-O-(4-formyl-3-methoxyphenyl)-α-D-neuraminate (9). To a stirred solution of compound (8) (900 mg, 5.92 mmol) in anhydrous tetrahydrofuran (35 mL) was added portionwise sodium hydride (288 mg of a 60% dispersion in mineral oil, 7.2 mmol) under a nitrogen atmosphere at room temperature. The resulting mixture was allowed to stir at room temperature for 2.5 h. The mixture was treated with compound (3) (2.33 g, 4.58 mmol) and the resulting mixture was stirred under a nitrogen atmosphere at room temperature for 115 h. The mixture was concentrated to dryness, the residue was diluted with ethyl acetate (40 mL), and washed with water (40 mL). The aqueous phase was extracted with ethyl acetate (3×40 mL), and combined organic phases were dried with magnesium sulfate, filtered, and the filtrate was concentrated to dryness. The residue was chromatographed (silica gel, 1:1 acetone-hexanes as eluting solvent) to afford pure compound (9) (1.23 g, 43%): $R_f$=0.31 (1:1 acetone-hexanes; UV, $H_2SO_4$).

$^1$H NMR ($CDCl_3$): (1.96 (s, 3H, NAc), 2.07, 2.09, 2.14, 2.18 (4 s, 12H, 4×OAc), 2.23–2.45 (m, 1H, H-3a), 2.74 (dd, 1H, $J_{3e,4}$ 5.9 Hz, $J_{3a,3e}$ 13.7 Hz, H-3e), 3.73 (s, 3H, $CO_2CH_3$), 3.93 (s, 3H, $OCH_3$), 4.12–4.22 (m, 2H), 4.25–4.30 (m, 1H), 4.60 (dd, 1H, J 1.8 Hz, J 12.6 Hz), 4.96–5.08 (m, 1H), 5.28–5.47 (m, 3H), 6.65 (d, 1H, J 3.0 Hz, ArH), 6.74 (dd, 1H, J 3.0 Hz, J 9.6 Hz, ArH), 7.82 (d, 1H, J 9.6 Hz, ArH), 10.33 (s, 1H, CHO).

Preparation of N-Acetyl-2-O-(4-formyl-3-methoxyphenyl)-α-D-neuraminic acid (10). A solution of compound (9) (751 mg, 1.20 mmol) in aqueous sodium hydroxide (20.0 mL of a 1.0 M solution, 20.0 mmol) was stirred at room temperature for 2 h. The resulting mixture was cooled to 0° C. and treated with methanol-washed Dowex 50W-X4 til pH 3. The mixture was filtered, the filtered resin was rinsed with water, and the filtrate was lyophilized to afford compound (10) (288 mg, 54%): $R_f$=0.34 (5:2:1 ethyl acetate-methanol-0.02% aqueous calcium chloride; UV, $H_2SO_4$).

$^1$H NMR ($D_2O$): (2.08 (s, 3H, NAc), 2.04–2.12 (m, 1H, H-3a), 2.87 (dd, 1H, $J_{3,4}$ 5.6 Hz, $J_{3a,3e}$ 15.0 Hz, H-3e), 3.60–3.68 (m, 2H), 3.81–3.95 (m, 4H), 3.93 (s, 3H, $OCH_3$), 4.23 (dd, 1H, J 3.7 Hz, J 11.2 Hz), 6.85 (dd, 1H, J 5.7 Hz, J 11.4 Hz, ArH), 6.97 (d, 1H, J 5.7 Hz, ArH), 7.75 (d, 1H, J 11.4 Hz, ArH), 10.0 (s, 1H, CHO).

EXAMPLE 4

Preparation of N-acetyl-2-O-[3-methoxy-4-(2-nitrovinyl)phenyl]-α-D-neuraminic Acid (11)

Figure 9:
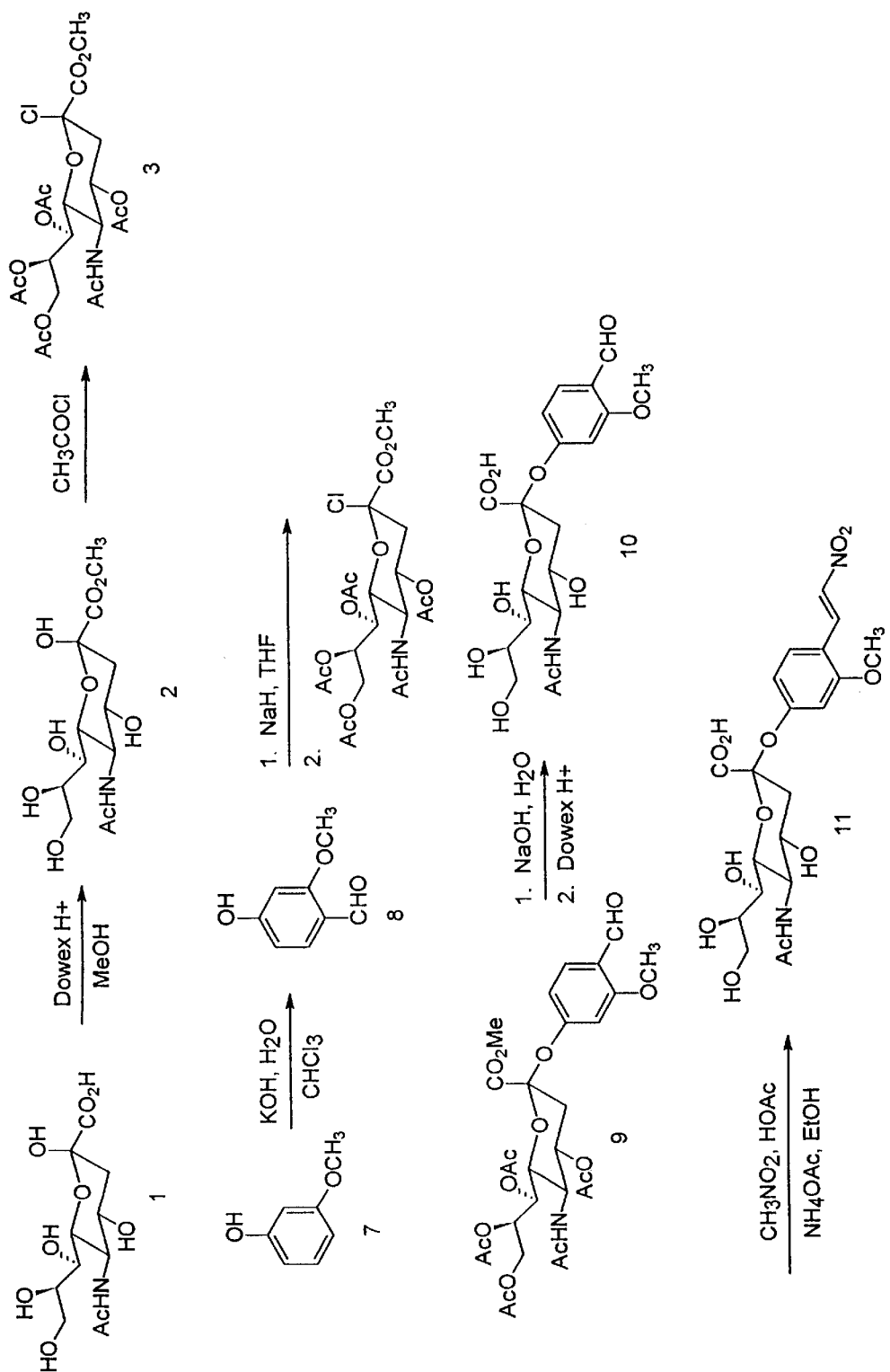
FIG. 9—shows an overall scheme for the preparation of N-acetyl-2-O-[3-methoxy-4-(2-nitrovinyl)phenyl]-α-D-neuraminic acid (11).

The overall reaction scheme is shown in FIG. 9. For the preparation of methyl N-acetyl-β-D-neuraminate (2), methyl N-acetyl-4,7,8,9-tetra-O-acetyl-2-chloro-2-deoxy-D-neuraminate (3), see the experimental details presented previously.

For the preparations of 4-hydroxy-2-methoxybenzaldehyde (8), methyl N-acetyl-4,7,8,9-tetra-O-acetyl-2-O-(4-formyl-3-methoxyphenyl)-α-D-neuraminate (9), and N-acetyl-2-O-(4-formyl-3-methoxyphenyl)-α-D-neuraminic acid (10), see the experimental details presented in Example 3.

To a stirred solution of compound (10) (120 mg, 0.27 mmol) in a mixture of ethanol (4.8 mL) and acetic acid (0.12 mL) was added ammonium acetate (120 mg, 1.56 mmol) and nitromethane (0.48 mL, 8.86 mmol) at room temperature. The reaction mixture was heated under reflux for 30 min, cooled to room temperature, and evaporated to dryness. The residue was chromatographed (silica gel, 5:2:1 ethyl acetate-methanol-0.02% aqueous calcium chloride as eluting solvent) to afford pure compound (11) (48 mg, 36%): $R_f$=0.64 (5:2:1 ethyl acetate-methanol-0.02% aqueous calcium chloride; UV, $H_2SO_4$).

$^1$H NMR ($D_2O$): (2.06 (s, 3H, NAc), 1.98–2.03 (m, 1H, H-3a), 2.88 (dd, 1H, $J_{3e,4}$ 5.1 Hz, $J_{3a,3e}$ 14.0 Hz, H-3e), 3.59–3.68 (m, 2H), 3.75–4.00 (m, 4H), 3.95 (s, 3H, $OCH_3$), 4.11 (dd, 1H, J 2.5 Hz, J 11.4 Hz), 6.82 (d, 1H, J 10.8 Hz, ArH), 6.95 (br s, 1H, ArH), 7.54 (d, 1H, J 10.8 Hz, ArH), 8.00 (d, 1H, J 13.5 Hz, H-vinylic), 8.22 (d, 1H, J 13.5 Hz, H-vinylic).

EXAMPLE 5

Preparation of Methyl N-acetyl-4,7,8,9-tetra-O-acetyl-2-O-(4-formyl-2-methoxyphenyl)-α-D-neuraminic Acid (12) and N-acetyl-2-O-(4-formyl-2-methoxyphenyl)-α-D-neuraminic Acid (13)

Figure 10:
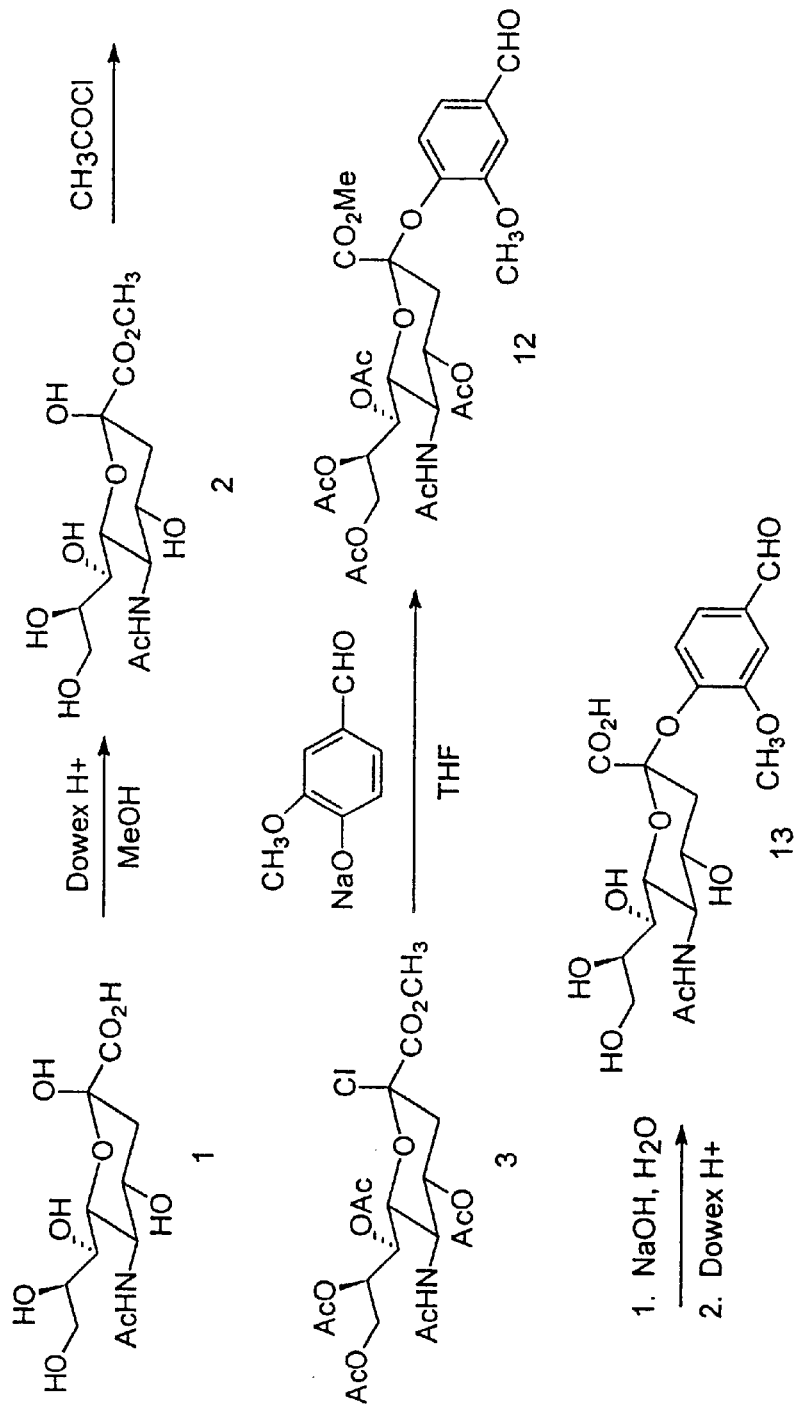
FIG. 10—shows an overall scheme for the preparation of methyl N-acetyl-4,7,8,9-tetra-O-acetyl-2-O-(4-formyl-2-methoxyphenyl)-α-D-neuraminic acid (12) and N-acetyl-2-O-(4-formyl-2-methoxyphenyl)-α-D-neuraminic acid (13).

The overall reaction scheme is shown in FIG. 10. For the preparation of methyl N-acetyl-β-D-neuraminate (2), methyl N-acetyl-4,7,8,9-tetra-O-acetyl-2-chloro-2-deoxy-D-neuraminate (3), see the experimental details presented previously.

Preparation of Methyl N-acetyl-4,7,8,9-tetra-O-acetyl-2-O-(4-formyl-2-methoxyphenyl)-α-D-neuraminic Acid (12). To a stirred solution of vanillin (4-hydroxy-3-methoxybenzaldehyde) (273 mg, 1.8 mmol) in anhydrous tetrahydrofuran (12.0 mL) was added portionwise sodium hydride (86 mg of a 60% dispersion in mineral oil, 2.2 mmol) under a nitrogen atmosphere at room temperature. The resulting mixture was allowed to stir at room temperature for 2.5 h. The mixture was treated with compound (3) (700 mg, 1.38 mmol) and the resulting mixture was stirred under a nitrogen atmosphere at room temperature for 68 h. The mixture was concentrated to dryness, the residue was diluted with ethyl acetate (25 mL), and washed with water (25 mL). The aqueous phase was extracted with ethyl acetate (3×25 mL), and combined organic phases were dried with magnesium sulfate, filtered, and the filtrate was concentrated to dryness. The residue was chromatographed (silica gel, chloroform, followed by ethyl acetate as eluting solvent) to afford pure compound (12) (322 mg, 38%): $R_f$=0.64 (1:8 acetone-ethyl acetate; UV, $H_2SO_4$).

$^1$H NMR (CDCl$_3$): (1.94 (s, 3H, NAc), 2.08, 2.09, 2.14, 2.19 (4 s, 12H, 4×OAc), 2.33 (ut, 1H, $J_{3a,3e}$=$J_{3a,4}$=13.5 Hz, H-3a), 2.82 (dd, 1H, $J_{3e,4}$5.4 Hz, H-3e), 3.70 (s, 3H, CO$_2$CH$_3$), 3.92 (s, 3H, OCH$_3$), 4.10–4.18 (m, 2H), 4.23–4.31 (m, 1H), 4.52 (br d, 1H, J 11.4 Hz), 4.97–5.12 (m, 1H), 5.20–5.28 (m, 1H), 5.30–5.40 (m, 2H), 7.32 (d, 1H, J9.0 Hz, ArH), 7.41–7.48 (m, 2H, 2×ArH), 9.92 (s, 1H, CHO).

Preparation of N-Acetyl-2-O-(4-formyl-2-methoxyphenyl)-α-D-neuraminic acid (13). A solution of compound (12) (236 mg, 0.38 mmol) in aqueous sodium hydroxide (6.0 mL of a 1.0 M solution, 6.0 mmol) was stirred at room temperature for 160 min. The resulting mixture was cooled to 0° C. and treated with methanol-washed Dowex 50W-X4 til pH 3. The mixture was filtered, the. filtered resin was rinsed with water, and the filtrate was lyophilized to afford compound (13) (152 mg, 91%): $R_f$=0.46 (5:2:1 ethyl acetate-methanol-0.02% aqueous calcium chloride; UV, $H_2SO_4$).

$^1$H NMR (D$_2$O): (2.08 (s, 3H, NAc), 2.03–2.12 (m, 1H, H-3a), 2.92 (dd, 1H, $J_{3e,4}$ 5.2 Hz, $J_{3a,3e}$ 13.9 Hz, H-3e), 3.54–3.70 (m, 2H), 3.80–4.20 (m, 5H), 3.92 (s, 3H, OCH$_3$), 7.48 (d, 1H, J 9.6 Hz, ArH), 7.52–7.60 (m, 2H, 2×ArH), 9.82 (s, 1H, CHO).

EXAMPLE 6

Preparation of N-acetyl-2-O-[2-methoxy-4-(2-nitrovinyl)phenyl]-α-D-neuraminic Acid (14)

Figure 11:
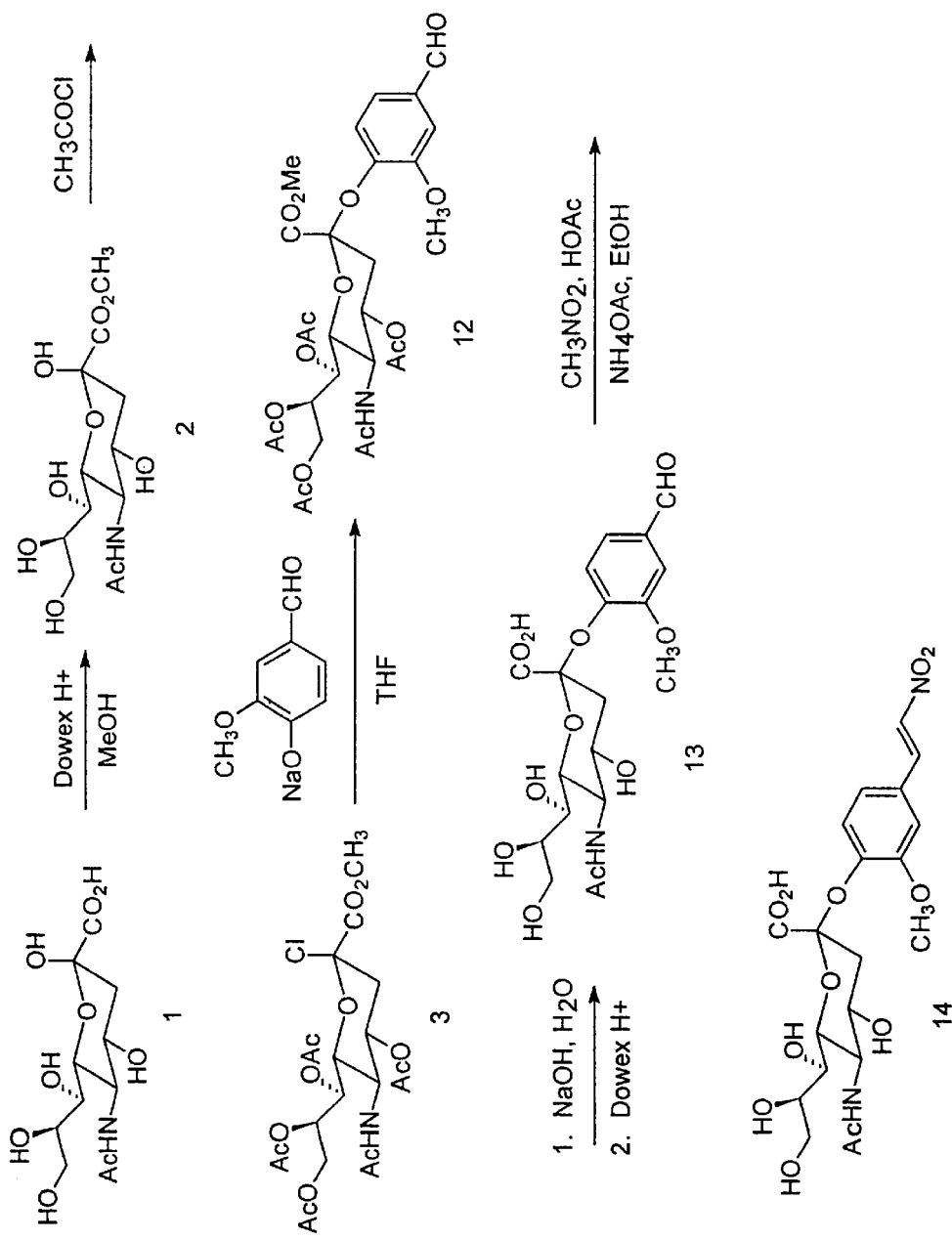
FIG. 11—shows an overall scheme for the preparation of N-acetyl-2-O-[2-methoxy-4-(2-nitrovinyl)phenyl]-α-D-neuraminic acid (14).

The overall reaction scheme is shown in FIG. 11. For the preparation of methyl N-acetyl-β-D-neuraminate (2), methyl N-acetyl-4,7,8,9-tetra-O-acetyl-2-chloro-2-deoxy-D-neuraminate (3), see the experimental details presented previously.

For the preparation of methyl N-acetyl-4,7,8,9-tetra-O-acetyl-2-O-(4-formyl-2-methoxyphenyl)-α-D-neuraminic acid (12) and N-acetyl-2-O-(4-formyl-2-methoxyphenyl)-α-D-neuraminic acid (13), see the experimental details presented in Example 5.

Preparation of N-Acetyl-2-O-[2-methoxy-4-(2-nitrovinyl)phenyl]-α-D-neuraminic acid (14). To a stirred solution of compound (13) (25 mg, 0.06 mmol) in a mixture of ethanol (2.0 mL) and acetic acid (0.02 mL) was added ammonium acetate (24 mg, 0.32 mmol) and nitromethane (0.10 mL, 1.9 mmol) at room temperature. The reaction mixture was heated under reflux for 30 min,. cooled to room temperature, and evaporated to dryness. The residue was chromatographed (silica gel, 5:2:1 ethyl acetate-methanol-0.02% aqueous calcium chloride as eluting solvent) to afford pure compound (14) (19 mg, 70%): $R_f$32 0.64 (5:2:1 ethyl acetate-methanol-0.02% aqueous calcium chloride; UV, $H_2SO_4$).

$^1$H NMR (D$_2$O): (2.07 (s, 3H, NAc), 1.97–2.04 (m, 1H, H-3a), 2.87 (dd, 1H, $J_{3e,4}$ 5.1 Hz, $J_{3a,3e}$ 14.0 Hz, H-3e), 3.54–3.69 (m, 2H), 3.81–4.05 (m, 5H), 3.93 (s, 3H, OCH$_3$), 7.45 (d, 1H, J 9.6 Hz, ArH), 7.48–7.55 (m, 2H, 2×ArH), 8.02 (d, 1H, J 13.3 Hz, H-vinylic), 8.20 (d, 1H, J 13.3 Hz, H-vinylic).

EXAMPLE 7

Preparation of N-acetyl-2-O-(5-bromo-4-chloroindol-3-yl)-α-D-neuraminic Acid (28)

Figure 12:
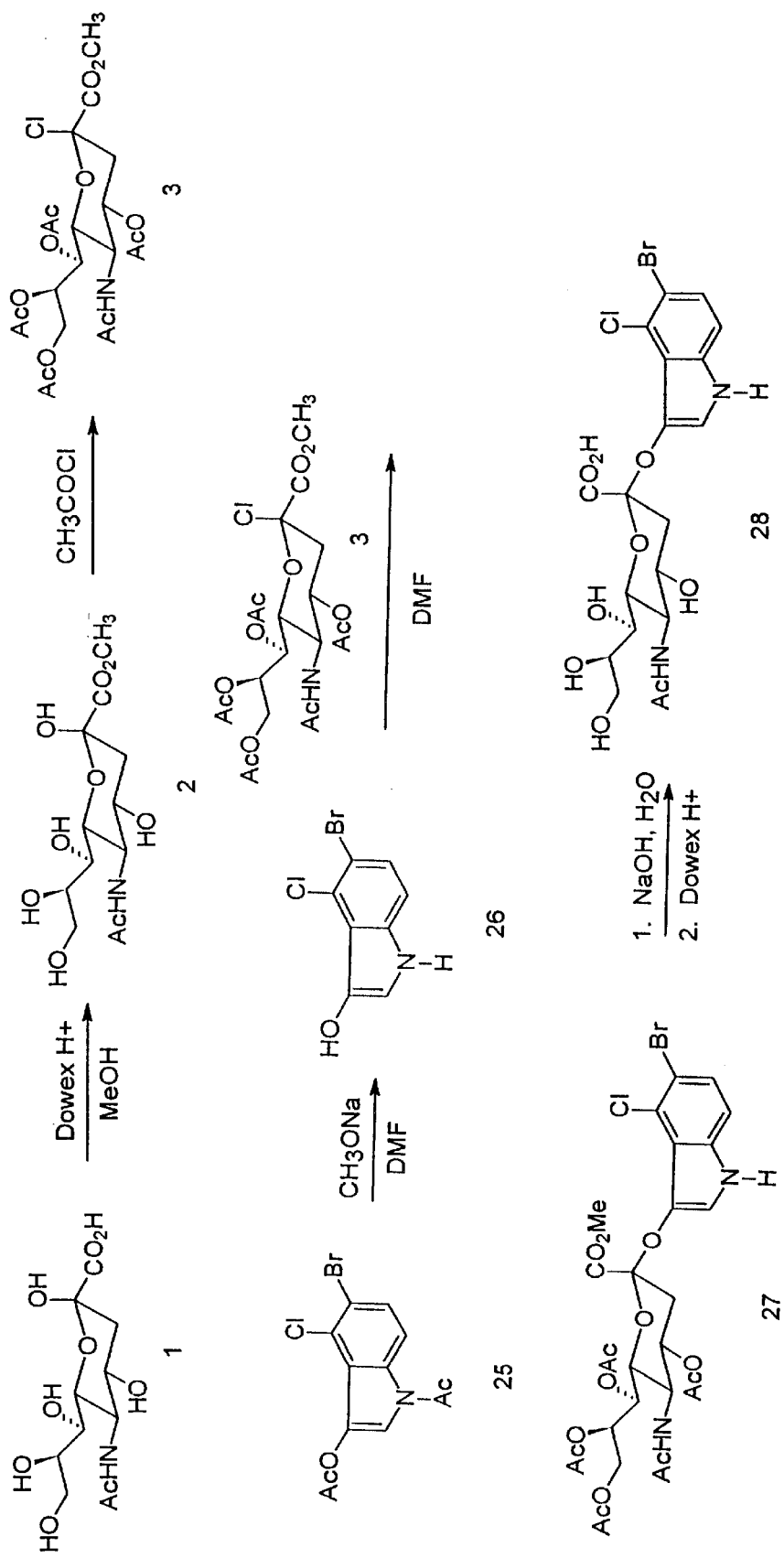
FIG. 12—shows the overall scheme for preparation of N-acetyl-2-O-(5-bromo-4-chloroindol-3-yl)-α-D-neuraminic acid (28).

The overall reaction scheme is shown in FIG. 12. For the preparation of methyl N-acetyl-β-D-neuraminate (2), methyl N-acetyl-4,7,8,9-tetra-O-acetyl-2-chloro-2-deoxy-D-neuraminate (3), see the experimental details presented previously.

reparation of 5-Bromo-4-chloro-3-hydroxyindole (26). To a stirred solution of 5-bromo-4-chloroindoxyl 1,3-diacetate (25) (1.0 g, 3.03 mmol) in anhydrous N,N-dimethylformamide (3 mL) was added sodium methoxide (270 mg, 5.00 mmol). The resulting dark-colored reaction mixture was degassed with nitrogen (g) for 30 min at room temperature.

Preparation of methyl N-acetyl-4,7,8,9-tetra-O-acetyl-2-O-(5-bromo-4-chloroindol-3-yl)-α-D-neuriminate (27). The reaction mixture of compound (26) in N,N-dimethylformamide was treated with stirring with compound (3) (238 mg, 0.468 mmol) at room temperature under a nitrogen atmosphere protected from light. After 16 h, the reaction mixture was concentrated under vacuum, coevaporated with xylenes (3×25 mL) to remove traces of N,N-dimethylformamide, treated with ethyl acetate (40 mL), and filtered. The filtrate was concentrated to a residue that was chromatographed (silica gel, 1:8 acetone-ethyl acetate as eluting solvent) to provide compound 27.

It should be understood that the examples and embodiments described herein are for illustrative purposes only and that various modifications or changes in light thereof will be suggested to persons skilled in the art and are to be included within the spirit and purview of this application and the scope of the appended claims.

References

Hirst, G. K. (1941) "The Agglutination of Red Blood Cells by Allontoic Fluid of Chick Embryos Infected with Influenza Virus," *Science* 94:22–23.

Crennell, S. J. , et al. (1993) "Crystal Structure of a Bacterial Sialidase (from *Salmonella typhimurium* LT2) Shows the Same Fold as an Influenza Virus Neuraminidase," *Proceedings of the National Academy of Science USA* 90(November):9852–9856.

Crennell, S., et al. (1994) "Crystal structure of Vibrio cholerae neuraminidase reveals dual lectin-like domains in addition to the catalytic domain," *Structure* 2(6):535–44.

Liu, C., et al. (1995) "Influenza type A virus neuraminidase does not play a role in viral entry, replication, assembly, or budding," *J. Virol.* 69:1099–1106.

Briselden, A. M., et al. (1992) "Sialidases (Neuraminidases) in bacterial vaginosis and bacterial vaginosis-associated microflora," *J. Clin. Microbiol.* 30:663–666.

Liljemark, W. F., et al. (1989) "Effect of neuraminidase on the adherence to salivary pellicle of *Streptococcus sangius* and *Streptpcoccus mitis*," *Caries Res.* 23:141–145.

Cross, G. A. and G. B. Takle (1993) "The surface trans-sialidase family of *Trypanosoma cruzi*," *Annu. Rev. Microbiol.* 47:385–411.

Cacalano, G. et al. (1992) "Production of the *Pseudomonas aeruginosa* Neuraminidase is increased under hyperosmolar conditions and is regulated by genes involved in alginate expression," *J. Clin. Invest.* 89:1866–1874.

Bratosin, D., et al. (1995) "Flow cytofluorometric analysis of young and senescent human erythrocytes probed with lectins—evidence that sialic acids control their life-span," *Glycoconj. J.* 12:258–267.

Bonten, E., et al. (1996) "Characterization of human lysosomal neuraminidase defines the molecular basis of the metabolic storage disorder sialidosis," *Genes & Devel.* 10:3156–3169.

Gornati, R., et al. (1997) "Activities of glycolipid glycosyltransferases and sialidases during the early development of *Xenopus laevis*," *Mol. Cell Biochem.* 166:117–124.

Lentz, M. R., R. G. Webster, G. M. Air (1987) "Site-Directed Mutation of the Active Site of Influenza Neuraminidase and Implications for the Catalytic Mechanism," *Biochemistry* 26:5351–5358.

Aamlid, K. H., G. Lee, B. V. Smith, A. C. Richardson, R. G. Price (1990) "New Colormetric Substrates for the Assay of Glycosidases," *Carbohydr. Res.* 205:c5–c9.

Baggett, N., B. J. Marsden (1982) "Reinvestigation of the Synthesis of 4-Methylcoumarin-7-yl 5-Acetamido-3,5-dideoxy-(-D-glycero-D-galacto-2-nonulopyranosidonic Acid, A Fluorimetric Substrate for Neuriminidase," *Carbohydr. Res.* 110:11–18.

Eschenfelder, V., R. Brossmer (1987) "Synthesis of p-Nitrophenyl 5-Acetamido-3,5-dideoxy-(-D-glycero-D-galacto-2-nonulopyranosidonic Acid, a Chromogenic Substrate for Sialidases," *Carbohydr. Res.* 162:294–297.

Eschenfelder, V., R. Brossmer, (1987) "5-Bromo-indol-3-yl 5-Acetamido-3,5-dideoxy-(-D-glycero-D-galactononulopyranosidonic Acid, a Novel Chromogenic Substrate for the Staining of Sialidase Activity," *Glycoconjugate J.* 4171–178.

Freudenberg, K., H. Resnik, H. Boesenberg, D. Rasenack (1952) "Das an der Verholzung Beteiligte Fermentsystem," *Chem. Ber.* 85:641–647.

Holmquist, L., R. Brossmer (1972) "Specificity of neuraminidase, synthesis and properties of the 2-aminoethyl α- and the 2-pyridyl α- and β-glycosides of N-acetyl-D-neuraminic acid," *Hoppe-Seyler's Z. Physiol. Chem.* 353:1346–1350.

Horwitz, J. P., J. Chua, R. J. Curby, A. J. Tomson, M. A. Darooge, B. E. Fisher, J. Mauricio, I. Klundt (1964) "Substrates for Cytochemical Demonstration of Enzyme Activity. I. Some Substituted 3-Indolyl-(-D-glycopyranosides," *J. Med. Chem.* 7:574–575.

de Kiewiet, T. E., H. Stephen (1931) "2-Hydroxy-4-methoxy- and 4-Hydroxy-2-methoxy-benzaldehydes," *J. Chem. Soc.* 133:84–85.

Kuhn, R., P. Lutz, D. L. MacDonald (1966) "Synthese anomerer Sialinsäure-methylketoside," *Chem. Ber.* 99:611–617.

Ley, A. N., R. J. Bowers, S. Wolfe (1988) "Indoxyl-(-D-glucuronide, a Novel Chromogenic Reagent for the Specific Detection and Enumeration of *Escherichia coli* in Environmental Samples," *Can. J. Microbiol.* 34:690–693.

Myers, R. W., R. T. Lee, Y. C. Lee, G. H. Thomas, L. W. Reynolds, Y. Uchida (1980) "The Synthesis of 4-Methylumbelliferyl α-Ketoside of N-Acetyl-Neuraminic Acid and Its Use in a Fluoromatic Assay for Neuraminidases," *Anal. Biochem.* 101:166–174.

Ogura, H., K. Furuhata, M. Itoh, Y. Shitori (1986) "Syntheses of 2-O-Glycosyl Derivatives of N-Acetyl-D-neuraminic Acid," *Carbohydr. Res.* 158:37–51.

Okamoto, K., T. Goto (1990) "Glycosidation of Sialic Acid," *Tetrahedron*, 46:5835–5857.

Patel, A., A. C. Richardson (1986) "3-Methoxy-4-(2-nitrovinyl)phenyl Glycosides as Potential Chromogenic Substrates for the Assay of Glycosidases," *Carbohydr. Res.* 146:241–249.

Paulsen, H., P. Matschulat, "Synthese von C-Glycosiden der N-Acetylneuraminsäure und weiteren Derivaten," *Liebigs Ann. Chem.* 487–495.

Robertson, A. (1927) "Syntheses of Glucosides. Part I. The Synthesis of Indican," *J Chem. Soc.* 1937–1943.

Tiemann, F., P. Koppe (1981) "Ueber die Darstellung von Protocatechualdehyd aus Brenzcatechin, sowie einige Derivate des Guajacols und Kreosols," *Chem Ber.* 14:2015–2028.

Warner, T. G., J. S. O'Brien (1979) "Synthesis of 2'-(4-Methylumbelliferyl)-(-D-N-acetylneuriminic Acid and Detection: of Skin Fibroblast Neuriminidase in Normal Humans and in Sialidosis ," *Biochemistry* 18:2783–2787.

What is claimed is:

1. A method of detecting the presence of a sialidase in a sample comprising contacting a chromogenic sialidase substrate compound comprising the formula of General Structure I or a composition comprising a chromogenic sialidase substrate of General Structure I and detecting a visible color change that indicates the presence of a sialidase, wherein the chromogenic sialidase substrate compound comprises:

General Structure I

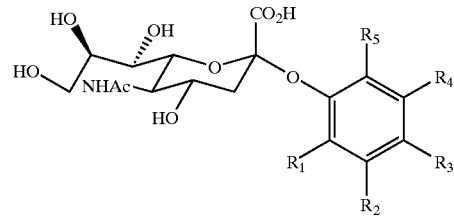

wherein $R_1$, $R_2$, $R_4$, or $R_5$ are substituents selected from the group consisting of H, $R_6$, Cl, Br, I, F, and $NO_2$, provided that at least two of said substituents are substituted with H;

$R_3$ is $CH=CHNO_2$,

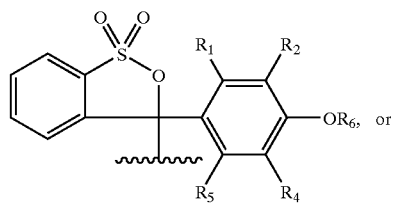

or

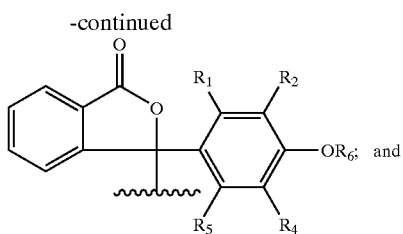

$R_6$ is H, $CH(CH_3)_2$, $(CH_2)_mCH_3$ and m is an integer from 0 to 3; or salts of said chromogenic sialidase substrate compounds.

2. The method according to claim 1, wherein $R_1$ and $R_2$, are H.

3. The method according to claim 1, wherein $R_1$ and $R_4$, are H.

4. The method according to claim 1, wherein $R_1$ and $R_5$, are H.

5. The method according to claim 1, wherein $R_2$ and $R_4$ are H.

6. The method according to claim 1, wherein $R_2$ and $R_5$, are H.

7. The method according to claim 1, wherein $R_4$ and $R_5$, are H.

8. The method according to claim 1, wherein $R_1$, $R_2$, and $R_5$ are H.

9. The method according to claim 1, wherein $R_1$, $R_4$, and $R_5$ are H.

10. The method according to claim 1, wherein $R_2$, $R_4$, and $R_5$ are H.

11. The method according to claim 1, wherein $R_1$, $R_2$, $R_4$, and $R_5$ are H.

12. The method according to claim 1, wherein R3 is $CH=CHNO_2$.

13. The method according to claim 1, wherein $R_3$ is

14. The method according to claim 1, wherein $R_3$ is

15. The method according to claim 1, wherein $R_6$ is H.

16. The method according to claim 1, wherein $R_6$ is $CH(CH_3)_2$.

17. The method according to claim 1, wherein $R_6$ is $(CH_2)_mCH_3$ wherein m is an integer from 0 to 3.

18. The method according to claim 17, wherein m is 0.

19. The method according to claim 17, wherein m is 1.

20. The method according to claim 17, wherein m is 2.

21. The method according to claim 17, wherein m is 3.

22. The method according to claim 1, wherein a chromogenic sialidase substrate compound comprising the formula of General Structure I is contacted.

23. The method according to claim 1, wherein a composition comprising a chromogenic sialidase substrate of General Structure I is contacted.

* * * * *

UNITED STATES PATENT AND TRADEMARK OFFICE
CERTIFICATE OF CORRECTION

| | |
|---|---|
| PATENT NO. | : 6,812,332 B2 |
| APPLICATION NO. | : 10/348668 |
| DATED | : November 2, 2004 |
| INVENTOR(S) | : Stephen C. Johnson, Ashraf Saeed and Ming Luo |

It is certified that error appears in the above-identified patent and that said Letters Patent is hereby corrected as shown below:

Title page,
Item 54, title "Chromogenic Substrates of Sialidase and Methods of Making and Using the Same "

should read

-- Methods of Detecting Bacterial, Viral, Protozoan, and Vertebrate Enzymes--

Title page,
Item 62 "Division of application No. 10/328,790, filed on Dec. 24, 2002, which is a division of application No. 09/651,622, filed on Aug. 3, 2000"

should read

--Division of application No. 10/328,790, filed on Dec. 24, 2002, which is a division of application No. 09/651,622, filed on Aug. 30, 2000--

Column 5,
Line 37 "$N(R_6)_2,$ "

should read

--$N(R_6)_2$;--

Column 7,
Line 25 "$CH_2PO_3R_6,$"

should read

--$CH_2PO_3R_8$--

Column 7,
Line 67 "where is an"

should read

--where $j$ is an--

UNITED STATES PATENT AND TRADEMARK OFFICE
CERTIFICATE OF CORRECTION

PATENT NO. : 6,812,332 B2
APPLICATION NO. : 10/348668
DATED : November 2, 2004
INVENTOR(S) : Stephen C. Johnson, Ashraf Saeed and Ming Luo It is certified that error appears in the above-identified patent and that said Letters Patent is hereby corrected as shown below:

Column 13,
Line 38 "Glycoconjugate .,"

should read

--Glycoconjugate J.,--

Column 14,
Line 46 "IEBX4023"

should read

--IBX4023--

Column 16,
Line 55 "Acid"

should read

--acid (6)--

Column 17,
Line 47 "N-acetyl-4.7.8.9-tetra"

should read

--N-acetyl-4,7,8,9-tetra--

Column 19,
Line 39 "the. filtered resin"

should read

--the filtered resin--

Column 20,
Line 3 "30 min,. cooled"

should read

--30 min, cooled--

UNITED STATES PATENT AND TRADEMARK OFFICE
CERTIFICATE OF CORRECTION

| | |
|---|---|
| PATENT NO. | : 6,812,332 B2 |
| APPLICATION NO. | : 10/348668 |
| DATED | : November 2, 2004 |
| INVENTOR(S) | : Stephen C. Johnson, Ashraf Saeed and Ming Luo |

It is certified that error appears in the above-identified patent and that said Letters Patent is hereby corrected as shown below:

Column 20,

Line 26 "reparation"

should read

--Preparation--

Column 20, Line 34:

"neuriminate"

should read

--neurminate--

Column 20, Line 6:

"*Streptpcoccus*"

should read

--*Streptococcus*--

Column 21, Line 36:

"Neuriminidase"

should read

--Neuraminidase--

Column 21,

Lines 34-35 "5-Acetamido-3,5-dideoxy-(-D-glycero-D-galactononulopyranosidonic Acid,"

should read

--5-Acetamido-3,5-dideoxy-α-D-glycero-D-galactononulopyranosidonic Acid,--

UNITED STATES PATENT AND TRADEMARK OFFICE
CERTIFICATE OF CORRECTION

PATENT NO. : 6,812,332 B2
APPLICATION NO. : 10/348668
DATED : November 2, 2004
INVENTOR(S) : Stephen C. Johnson, Ashraf Saeed and Ming Luo It is certified that error appears in the above-identified patent and that said Letters Patent is hereby corrected as shown below:

Column 21,

Lines 39-40 "p-Nitrophenyl 5-Acetamido-3,5-dideoxy-(-D-glycero-D-galactononulopyranosidonic Acid,"

should read

--p-Nitrophenyl 5-Acetamido-3,5-dideoxy-α-D-glycero-D-galactononulopyranosidonic Acid,--

Column 21,

Lines 42-44 "5-Bromo-indol-3yl-5-Acetamido-3,5-dideoxy-(-D-glycero-D-galactononulopyranosidonic Acid,"

should read

--5-Bromo-indol-3yl-5-Acetamido-3,5-dideoxy- α-D-glycero-D-galactononulopyranosidonic Acid,--

Signed and Sealed this

Fifth Day of June, 2007

JON W. DUDAS
*Director of the United States Patent and Trademark Office*